(12) United States Patent
Atabai et al.

(10) Patent No.: US 10,005,838 B2
(45) Date of Patent: Jun. 26, 2018

(54) MILK FAT GLOBULE EPIDERMAL GROWTH FACTOR 8 REGULATES FATTY ACID UPTAKE

(71) Applicant: REGENTS OF THE UNIVERSITY OF CALIFORNIA, Oakland, CA (US)

(72) Inventors: Kamran Atabai, San Francisco, CA (US); Sayyed M. Amin Khalifeh-Soltani, San Francisco, CA (US); Dean Sheppard, Oakland, CA (US); Amha Atakilit, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 60 days.

(21) Appl. No.: 14/905,065

(22) PCT Filed: Jul. 17, 2014

(86) PCT No.: PCT/US2014/047061
§ 371 (c)(1),
(2) Date: Jan. 14, 2016

(87) PCT Pub. No.: WO2015/009948
PCT Pub. Date: Jan. 22, 2015

(65) Prior Publication Data
US 2016/0152710 A1 Jun. 2, 2016

Related U.S. Application Data

(60) Provisional application No. 61/856,475, filed on Jul. 19, 2013, provisional application No. 61/873,134, filed on Sep. 3, 2013.

(51) Int. Cl.
| | |
|---|---|
| *A61K 39/395* | (2006.01) |
| *C07K 16/28* | (2006.01) |
| *A61K 38/17* | (2006.01) |
| *A23G 4/12* | (2006.01) |
| *A23L 2/52* | (2006.01) |
| *A23L 2/66* | (2006.01) |
| *A23K 20/147* | (2016.01) |
| *A61K 38/18* | (2006.01) |
| *A23L 33/18* | (2016.01) |
| *G01N 33/68* | (2006.01) |
| *A61K 39/00* | (2006.01) |

(52) U.S. Cl.
CPC ............ *C07K 16/2848* (2013.01); *A23G 4/12* (2013.01); *A23K 20/147* (2016.05); *A23L 2/52* (2013.01); *A23L 2/66* (2013.01); *A23L 33/18* (2016.08); *A61K 38/1709* (2013.01); *A61K 38/1808* (2013.01); *C07K 16/2839* (2013.01); *G01N 33/6893* (2013.01); *A61K 2039/505* (2013.01); *C07K 2317/24* (2013.01); *C07K 2317/76* (2013.01); *G01N 2800/02* (2013.01); *G01N 2800/044* (2013.01)

(58) Field of Classification Search
None
See application file for complete search history.

(56) References Cited

U.S. PATENT DOCUMENTS

| | | | | |
|---|---|---|---|---|
| 2006/0127407 | A1* | 6/2006 | Chen .................. | C07K 16/2839 424/178.1 |
| 2008/0020979 | A1* | 1/2008 | Rapraeger ............ | C07K 14/705 514/1.9 |
| 2009/0280118 | A1* | 11/2009 | Sheppard ........... | C07K 16/2839 424/133.1 |

FOREIGN PATENT DOCUMENTS

| | | |
|---|---|---|
| WO | 2006/014678 A2 | 2/2006 |
| WO | 2011/069987 A1 | 6/2011 |
| WO | 2012/149254 A2 | 11/2012 |
| WO | 2012/170021 A1 | 12/2012 |

OTHER PUBLICATIONS

Tentori et al. The integrin antagonist Cilengitide increases the antitumor activity of temozolomide against malignant melanoma. Oncology Reports 19: 1039-1043, 2008 (Year: 2008).*
Dennis and Solnordal. Acute pulmonary oedema in pregnant women. Anaesthesia 2012, 67, 646-659 (Year: 2012).*
Santulli et al . Studies with an orally bioavailable alpha V integrin antagonist in animal models of ocular vasculopathy: retinal neovascularization in mice and retinal vascular permeability in diabetic rats. J Pharmacol Exp Ther. Mar. 2008;324(3):894-901 (Year : 2008).*
Zheng et al. CD11b regulates obesity-induced insulin resistance via limiting alternative activation and proliferation of adipose tissue macrophages. Proc Natl Acad Sci U S A. Dec. 29, 2015;112(52):E7239-48. (Year: 2015).*
Zeyda et al. Human adipose tissue macrophages are of an anti-inflammatory phenotype but capable of excessive pro-inflammatory mediator production. International Journal of Obesity (2007) 31, 1420-1428 (Year: 2007).*
Bu et al., "Milk fat globule-EGF factor 8/lactahedrin plays a crucial role in maintenance and repair of murine intestinal epithelium," *J. Clin. Invest.*, 117(12):3673-3683 (Dec. 2012).
Khalifeh-Soltani et al., "Mfge8 promotes obesity by mediating the uptake of dietary fats and serum fatty acids," *Nat. Med.*, 20:175-183 (Feb. 2014) ePub Jan. 19.
International Search Report and Written Opinion from PCT/US2014/047061, dated Dec. 15, 2014.

* cited by examiner

*Primary Examiner* — Maher M Haddad
(74) *Attorney, Agent, or Firm* — Kilpatrick Townsend & Stockton LLP

(57) ABSTRACT

Methods and compositions for regulating fatty acid uptake and/or decreasing gastric motility in an animal are provided. The method comprises administering an antagonist of integrin $\alpha_v\beta_3$ or $\alpha_v\beta_5$ to an animal in an amount sufficient to reduce fatty acid uptake in the animal, thereby reducing fatty acid uptake in the animal. In some embodiments, the antagonist is an antibody. Also provided is a method of increasing fatty acid uptake and/or gastric motility in an animal.

6 Claims, 14 Drawing Sheets

SEQUENCE LISTING

```
<160> NUMBER OF SEQ ID NOS: 7

<210> SEQ ID NO 1
<211> LENGTH: 335
<212> TYPE: PRT
<213> ORGANISM: Homo sapiens
<220> FEATURE:
<223> OTHER INFORMATION: human mature milk fat globule epidermal
      growth factor 8 (MFGE8), lactadherin isoform b, O-acetyl
      disialoganglioside synthase (OAAcGD3S), breast epithelial
      antigen BA46, medin, sperm associated antigen 10 (SPAG10),
      sperm surface protein hP47

<400> SEQUENCE: 1

Met Pro Arg Pro Arg Leu Leu Ala Ala Leu Cys Gly Ala Leu Leu Cys
 1               5                  10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
        35                  40                  45

Val Phe Pro Ser Tyr Thr Cys Thr Cys Leu Lys Gly Tyr Ala Gly Asn
    50                  55                  60

His Cys Glu Thr Lys Cys Val Glu Pro Leu Gly Leu Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
```

```
                275                 280                 285
Leu Gln Ile Phe Pro Gly Asn Trp Asp Asn His Ser His Lys Lys Asn
    290                 295                 300

Leu Phe Glu Thr Pro Ile Leu Ala Arg Tyr Val Arg Ile Leu Pro Val
305                 310                 315                 320

Ala Trp His Asn Arg Ile Ala Leu Arg Leu Glu Leu Leu Gly Cys
                325                 330                 335
```

<210> SEQ ID NO 2
<211> LENGTH: 387
<212> TYPE: PRT
<213> ORGANISM: Homo sapiens
<220> FEATURE:
<223> OTHER INFORMATION: human milk fat globule epidermal growth
      factor 8 preprotein (MFGE8), lactadherin isoform a preproprotein,
      O-acetyl disialoganglioside synthase (OAAcGD3S), breast epithelial
      antigen BA46, sperm surface protein hP47, SPAG10

<400> SEQUENCE: 2

```
Met Pro Arg Pro Arg Leu Leu Ala Ala Leu Cys Gly Ala Leu Leu Cys
 1                5                  10                  15

Ala Pro Ser Leu Leu Val Ala Leu Asp Ile Cys Ser Lys Asn Pro Cys
                20                  25                  30

His Asn Gly Gly Leu Cys Glu Glu Ile Ser Gln Glu Val Arg Gly Asp
            35                  40                  45

Val Phe Pro Ser Tyr Thr Cys Thr Cys Leu Lys Gly Tyr Ala Gly Asn
    50                  55                  60

His Cys Glu Thr Lys Cys Val Glu Pro Leu Gly Leu Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
    115                 120                 125

Gln Val Asn Leu Leu Arg Arg Met Trp Val Thr Gly Val Val Thr Gln
130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
    195                 200                 205

Pro Thr Ser Cys His Thr Ala Cys Thr Leu Arg Phe Glu Leu Leu Gly
210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
    275                 280                 285

Leu Gln Val Asp Leu Gly Ser Ser Lys Glu Val Thr Gly Ile Ile Thr
```

```
                290                 295                 300
Gln Gly Ala Arg Asn Phe Gly Ser Val Gln Phe Val Ala Ser Tyr Lys
305                 310                 315                 320

Val Ala Tyr Ser Asn Asp Ser Ala Asn Trp Thr Glu Tyr Gln Asp Pro
                325                 330                 335

Arg Thr Gly Ser Ser Lys Ile Phe Pro Gly Asn Trp Asp Asn His Ser
                340                 345                 350

His Lys Lys Asn Leu Phe Glu Thr Pro Ile Leu Ala Arg Tyr Val Arg
                355                 360                 365

Ile Leu Pro Val Ala Trp His Asn Arg Ile Ala Leu Arg Leu Glu Leu
370                 375                 380

Leu Gly Cys
385

<210> SEQ ID NO 3
<211> LENGTH: 463
<212> TYPE: PRT
<213> ORGANISM: Mus musculus
<220> FEATURE:
<223> OTHER INFORMATION: mouse milk fat globule epidermal growth
      factor 8 (Mfge8, MFG-E8) long form, lactadherin isoform 1
      precursor, sperm surface protein SP47 (MP47, P47), EGF/Factor
      VIII, Mfgm

<400> SEQUENCE: 3

Met Gln Val Ser Arg Val Leu Ala Ala Leu Cys Gly Met Leu Leu Cys
1               5                   10                  15

Ala Ser Gly Leu Phe Ala Ala Ser Gly Asp Phe Cys Asp Ser Ser Leu
                20                  25                  30

Cys Leu Asn Gly Gly Thr Cys Leu Thr Gly Gln Asp Asn Asp Ile Tyr
                35                  40                  45

Cys Leu Cys Pro Glu Gly Phe Thr Gly Leu Val Cys Asn Glu Thr Glu
                50                  55                  60

Arg Gly Pro Cys Ser Pro Asn Pro Cys Tyr Asn Asp Ala Lys Cys Leu
65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Glu Thr Asn
                100                 105                 110

Tyr Tyr Asn Leu Asp Gly Glu Tyr Met Phe Thr Thr Ala Val Pro Asn
                115                 120                 125

Thr Ala Val Pro Thr Pro Ala Pro Thr Pro Asp Leu Ser Asn Asn Leu
                130                 135                 140

Ala Ser Arg Cys Ser Thr Gln Leu Gly Met Glu Gly Gly Ala Ile Ala
145                 150                 155                 160

Asp Ser Gln Ile Ser Ala Ser Ser Val Tyr Met Gly Phe Met Gly Leu
                165                 170                 175

Gln Arg Trp Gly Pro Glu Leu Ala Arg Leu Tyr Arg Thr Gly Ile Val
                180                 185                 190

Asn Ala Trp Thr Ala Ser Asn Tyr Asp Ser Lys Pro Trp Ile Gln Val
                195                 200                 205

Asn Leu Leu Arg Lys Met Arg Val Ser Gly Val Met Thr Gln Gly Ala
                210                 215                 220

Ser Arg Ala Gly Arg Ala Glu Tyr Leu Lys Thr Phe Lys Val Ala Tyr
225                 230                 235                 240

Ser Leu Asp Gly Arg Lys Phe Glu Phe Ile Gln Asp Glu Ser Gly Gly
```

```
                    245                 250                 255
Asp Lys Glu Phe Leu Gly Asn Leu Asp Asn Asn Ser Leu Lys Val Asn
                260                 265                 270

Met Phe Asn Pro Thr Leu Glu Ala Gln Tyr Ile Lys Leu Tyr Pro Val
            275                 280                 285

Ser Cys His Arg Gly Cys Thr Leu Arg Phe Glu Leu Leu Gly Cys Glu
        290                 295                 300

Leu His Gly Cys Ser Glu Pro Leu Gly Leu Lys Asn Asn Thr Ile Pro
305                 310                 315                 320

Asp Ser Gln Met Ser Ala Ser Ser Tyr Lys Thr Trp Asn Leu Arg
                325                 330                 335

Ala Phe Gly Trp Tyr Pro His Leu Gly Arg Leu Asp Asn Gln Gly Lys
                340                 345                 350

Ile Asn Ala Trp Thr Ala Gln Ser Asn Ser Ala Lys Glu Trp Leu Gln
                355                 360                 365

Val Asp Leu Gly Thr Gln Arg Gln Val Thr Gly Ile Ile Thr Gln Gly
                370                 375                 380

Ala Arg Asp Phe Gly His Ile Gln Tyr Val Ala Ser Tyr Lys Val Ala
385                 390                 395                 400

His Ser Asp Asp Gly Val Gln Trp Thr Val Tyr Glu Glu Gln Gly Ser
                405                 410                 415

Ser Lys Val Phe Gln Gly Asn Leu Asp Asn Asn Ser His Lys Lys Asn
                420                 425                 430

Ile Phe Glu Lys Pro Phe Met Ala Arg Tyr Val Arg Val Leu Pro Val
                435                 440                 445

Ser Trp His Asn Arg Ile Thr Leu Arg Leu Glu Leu Leu Gly Cys
                450                 455                 460

<210> SEQ ID NO 4
<211> LENGTH: 331
<212> TYPE: PRT
<213> ORGANISM: Artificial Sequence
<220> FEATURE:
<223> OTHER INFORMATION: synthetic E1E2D1 mouse milk fat globule
      epidermal growth factor 8 (Mfge8) long construct (lacking
      second discoidin domain)

<400> SEQUENCE: 4

Met Gln Val Ser Arg Val Leu Ala Ala Leu Cys Gly Met Leu Leu Cys
1               5                   10                  15

Ala Ser Gly Leu Phe Ala Ala Ser Gly Asp Phe Cys Asp Ser Ser Leu
                20                  25                  30

Cys Leu Asn Gly Gly Thr Cys Leu Thr Gly Gln Asp Asn Asp Ile Tyr
            35                  40                  45

Cys Leu Cys Pro Glu Gly Phe Thr Gly Leu Val Cys Asn Glu Thr Glu
        50                  55                  60

Arg Gly Pro Cys Ser Pro Asn Pro Cys Tyr Asn Asp Ala Lys Cys Leu
65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Glu Thr Asn
            100                 105                 110

Tyr Tyr Asn Leu Asp Gly Glu Tyr Met Phe Thr Thr Ala Val Pro Asn
        115                 120                 125

Thr Ala Val Pro Thr Pro Ala Pro Thr Pro Asp Leu Ser Asn Asn Leu
130                 135                 140
```

```
Ala Ser Arg Cys Ser Thr Gln Leu Gly Met Glu Gly Ala Ile Ala
145                 150                 155                 160

Asp Ser Gln Ile Ser Ala Ser Val Tyr Met Gly Phe Met Gly Leu
                165                 170                 175

Gln Arg Trp Gly Pro Glu Leu Ala Arg Leu Tyr Arg Thr Gly Ile Val
            180                 185                 190

Asn Ala Trp Thr Ala Ser Asn Tyr Asp Ser Lys Pro Trp Ile Gln Val
                195                 200                 205

Asn Leu Leu Arg Lys Met Arg Val Ser Gly Val Met Thr Gln Gly Ala
            210                 215                 220

Ser Arg Ala Gly Arg Ala Glu Tyr Leu Lys Thr Phe Lys Val Ala Tyr
225                 230                 235                 240

Ser Leu Asp Gly Arg Lys Phe Glu Phe Ile Gln Asp Glu Ser Gly Gly
                245                 250                 255

Asp Lys Glu Phe Leu Gly Asn Leu Asp Asn Asn Ser Leu Lys Val Asn
                260                 265                 270

Met Phe Asn Pro Thr Leu Glu Ala Gln Tyr Ile Lys Leu Tyr Pro Val
            275                 280                 285

Ser Cys His Arg Gly Cys Thr Leu Arg Phe Glu Leu Leu Gly Cys Lys
            290                 295                 300

Pro Phe Met Ala Arg Tyr Val Arg Val Leu Pro Val Ser Trp His Asn
305                 310                 315                 320

Arg Ile Thr Leu Arg Leu Glu Leu Leu Gly Cys
                325                 330

<210> SEQ ID NO 5
<211> LENGTH: 431
<212> TYPE: PRT
<213> ORGANISM: Bos taurus
<220> FEATURE:
<223> OTHER INFORMATION: bovine milk fat globule epidermal growth
      factor 8 (Mfge8, MFG-E8), lactadherin, sperm surface protein
      SP47 (BP47), MGP57/53, PAS-6/PAS-7 glycoprotein, componenets
      15/16, MFGM

<400> SEQUENCE: 5

Met Pro Cys Pro Arg Leu Leu Ala Ala Leu Cys Gly Ala Leu Phe Cys
1               5                   10                  15

Ser Ser Gly Leu Phe Ala Phe Ser Gly Asp Phe Cys Asp Ser Ser Gln
                20                  25                  30

Cys Leu His Gly Gly Thr Cys Leu Leu Asn Glu Asp Arg Thr Pro Pro
            35                  40                  45

Phe Tyr Cys Leu Cys Pro Glu Gly Phe Thr Gly Leu Leu Cys Asn Glu
50                  55                  60

Thr Glu His Gly Pro Cys Phe Pro Asn Pro Cys His Asn Asp Ala Glu
65                  70                  75                  80

Cys Gln Val Thr Asp Asp Ser His Arg Gly Asp Val Phe Ile Gln Tyr
                85                  90                  95

Ile Cys Lys Cys Pro Leu Gly Tyr Val Gly Ile His Cys Glu Thr Thr
            100                 105                 110

Cys Thr Ser Pro Leu Gly Met Gln Thr Gly Ala Ile Ala Asp Ser Gln
            115                 120                 125

Ile Ser Ala Ser Ser Met His Leu Gly Phe Met Gly Leu Gln Arg Trp
130                 135                 140

Ala Pro Glu Leu Ala Arg Leu His Gln Thr Gly Ile Val Asn Ala Trp
145                 150                 155                 160
```

Thr Ser Gly Asn Tyr Asp Lys Asn Pro Trp Ile Gln Val Asn Leu Met
            165                 170                 175

Arg Lys Met Trp Val Thr Gly Val Val Thr Gln Gly Ala Ser Arg Ala
        180                 185                 190

Gly Ser Ala Glu Tyr Leu Lys Thr Phe Lys Val Ala Tyr Ser Thr Asp
        195                 200                 205

Gly Arg Gln Phe Gln Phe Ile Gln Val Ala Gly Arg Ser Gly Asp Lys
        210                 215                 220

Ile Phe Ile Gly Asn Val Asn Asn Ser Gly Leu Lys Ile Asn Leu Phe
225                 230                 235                 240

Asp Thr Pro Leu Glu Thr Gln Tyr Val Arg Leu Val Pro Ile Ile Cys
            245                 250                 255

His Arg Gly Cys Thr Leu Arg Phe Glu Leu Leu Gly Cys Glu Leu Asn
        260                 265                 270

Gly Cys Thr Glu Pro Leu Gly Leu Lys Asp Asn Thr Ile Pro Asn Lys
        275                 280                 285

Gln Ile Thr Ala Ser Ser Tyr Tyr Lys Thr Trp Gly Leu Ser Ala Phe
        290                 295                 300

Ser Trp Phe Pro Tyr Tyr Ala Arg Leu Asp Asn Gln Gly Lys Phe Asn
305                 310                 315                 320

Ala Trp Thr Ala Gln Thr Asn Ser Ala Ser Glu Trp Leu Gln Ile Asp
            325                 330                 335

Leu Gly Ser Gln Lys Arg Val Thr Gly Ile Ile Thr Gln Gly Ala Arg
        340                 345                 350

Asp Phe Gly His Ile Gln Tyr Val Ala Ala Tyr Arg Val Ala Tyr Gly
        355                 360                 365

Asp Asp Gly Val Thr Trp Thr Glu Tyr Lys Asp Pro Gly Ser Ser Glu
        370                 375                 380

Ser Lys Ile Phe Pro Gly Asn Met Asp Asn Asn Ser His Lys Lys Asn
385                 390                 395                 400

Ile Phe Glu Thr Pro Phe Gln Ala Arg Phe Val Arg Ile Gln Pro Val
            405                 410                 415

Ala Trp His Asn Arg Ile Thr Leu Arg Val Glu Leu Leu Gly Cys
        420                 425                 430

<210> SEQ ID NO 6
<211> LENGTH: 426
<212> TYPE: PRT
<213> ORGANISM: Capra hircus
<220> FEATURE:
<223> OTHER INFORMATION: goat milk fat globule epidermal growth
      factor 8 (Mfge8, MFG-E8)

<400> SEQUENCE: 6

Met Pro Ser Pro Arg Leu Leu Ala Ala Leu Cys Gly Ala Leu Phe Cys
1                   5                   10                  15

Ala Ser Gly Leu Phe Ala Phe Ser Gly Asp Leu Cys Asp Ser Ser Gln
            20                  25                  30

Cys Leu His Gly Gly Thr Cys Leu Leu Asn Glu Glu Lys Thr Pro Pro
        35                  40                  45

Phe Tyr Cys Leu Cys Pro Glu Gly Phe Thr Gly Leu Leu Cys Asn Glu
        50                  55                  60

Thr Glu Tyr Gly Pro Cys Phe Pro Asn Pro Cys His Asn Asp Ala Glu
65                  70                  75                  80

Cys Gln Val Thr Asp Thr Leu Arg Gly Asp Val Phe Thr His Tyr Ile

```
                  85                  90                  95
Cys Lys Cys Pro Leu Gly Tyr Val Gly Thr His Cys Glu Ser Thr Cys
            100                 105                 110

Thr Ser Pro Leu Gly Met Gln Thr Gly Ala Ile Ala Asp Ser Gln Ile
        115                 120                 125

Ser Ala Ser Ser Met His Leu Gly Phe Met Gly Leu Gln Arg Trp Ala
    130                 135                 140

Pro Glu Leu Ala Arg Leu Tyr Gln Thr Gly Ile Val Asn Ala Trp Thr
145                 150                 155                 160

Ser Ser Asn Tyr Asp Lys Asn Pro Trp Ile Gln Val Asn Leu Leu Arg
            165                 170                 175

Lys Met Trp Val Thr Gly Val Val Thr Gln Gly Ala Ser Arg Ala Gly
            180                 185                 190

Ser Ala Glu Tyr Val Lys Thr Phe Lys Val Ala Tyr Ser Asn Asp Gly
        195                 200                 205

His Gln Phe Gln Phe Ile Gln Ala Ala Gly Gln Leu Gly Glu Lys Val
    210                 215                 220

Arg Asn Asn Ser Gly Leu Lys Ile Asn Leu Phe Asp Ser Pro Leu Glu
225                 230                 235                 240

Thr Gln Tyr Val Arg Leu Val Pro Ile Ile Cys Arg Arg Gly Cys Thr
            245                 250                 255

Leu Arg Phe Glu Leu Leu Gly Cys Glu Leu Asp Gly Cys Thr Glu Pro
            260                 265                 270

Leu Gly Leu Lys Asp Asn Thr Ile Pro Asn Lys Gln Ile Thr Ala Ser
        275                 280                 285

Ser Tyr Tyr Lys Thr Trp Gly Leu Ser Ala Phe Ser Trp Phe Pro Tyr
    290                 295                 300

Tyr Ala Arg Leu Asp Asn Trp Gly Lys Phe Asn Ala Trp Thr Ala Gln
305                 310                 315                 320

Thr Asn Ser Ala Ser Glu Trp Leu Gln Ile Asp Leu Gly Ser Gln Lys
            325                 330                 335

Arg Val Thr Gly Ile Ile Thr Gln Gly Ala Arg Asp Phe Gly His Ile
            340                 345                 350

Gln Tyr Val Ala Ala Tyr Arg Val Ala Tyr Ser Asp Asp Gly Val Thr
        355                 360                 365

Trp Thr Glu Tyr Lys Asp Pro Glu Thr Ser Lys Ser Lys Ile Phe Pro
    370                 375                 380

Gly Asn Met Asp Asn Asn Ser His Lys Lys Asn Ile Phe Glu Val Pro
385                 390                 395                 400

Phe Gln Ala Arg Phe Val Arg Ile Gln Pro Val Ala Trp His Asn Arg
            405                 410                 415

Ile Thr Leu Arg Val Glu Leu Leu Gly Cys
            420                 425

<210> SEQ ID NO 7
<211> LENGTH: 6
<212> TYPE: PRT
<213> ORGANISM: Artificial Sequence
<220> FEATURE:
<223> OTHER INFORMATION: synthetic polyhistidine affinity purification
      fusion domain, detection domain, His6

<400> SEQUENCE: 7

His His His His His His
1               5
```

MILK FAT GLOBULE EPIDERMAL GROWTH FACTOR 8 REGULATES FATTY ACID UPTAKE

CROSS-REFERENCES TO RELATED APPLICATIONS

This application is a National Stage entry of International Appl. No. PCT/US2014/047061, filed Jul. 17, 2014, which claims the benefit of U.S. Provisional Application No. 61/856,475, filed Jul. 19, 2013 and U.S. Provisional Application No. 61/873,134, filed Sep. 3, 2013, the disclosures of each are incorporated herein in their entireties for all purposes.

REFERENCE TO A SEQUENCE LISTING, A TABLE, OR A COMPUTER PROGRAM LISTING APPENDIX SUBMITTED AS AN ASCII TEXT FILE

This application includes a Sequence Listing as a text file named "081906-215420US-0969191_ST25.txt", created on Jan. 12, 2016, and containing 21,670 bytes. The material contained in this text file is incorporated by reference in its entirety for all purposes.

BACKGROUND OF THE INVENTION

Obesity is a central feature of the metabolic syndrome, which leads to significant morbidity and mortality by increasing the risk of diabetes and cardiovascular disease. The absorption of dietary triglycerides with subsequent storage in adipose tissue is a key step in the development of obesity (Berk, P. D., et al., *J Biol Chem* 274, 28626-28631 (1999); Berk, P. D., et al., *J Biol Chem* 272, 8830-8835 (1997)). Under physiological conditions, cellular uptake of fatty acids occurs primarily through protein-mediated pathways consisting of a number of fatty acid transporters expressed in tissue-specific patterns (Stump, D. D., Fan, X. & Berk, P. D., *J Lipid Res* 42, 509-520 (2001); Anderson, C. M. & Stahl, A., *Mol Aspects Med* 34, 516-528 (2013)). Translocation of these transporters from the cytosol to the cell membrane is the major mechanism through which the rate of fatty acid uptake can be acutely regulated in response to dietary and metabolic cues (Stahl, A. et al., *Developmental cell* 2, 477-488 (2002); Luiken, J. J., et al., *Am J Physiol Endocrinol Metab* 282, E491-495 (2002); Luiken, J. J., et al., *Diabetes* 52, 1627-1634 (2003)). Fatty acid transporter translocation is regulated systemically by hormones and locally by muscle contraction (Stahl, A. et al., *Developmental cell* 2, 477-488 (2002); Luiken, J. J., et al., *Am J Physiol Endocrinol Metab* 282, E491-495 (2002); Luiken, J. J., et al., *Diabetes* 52, 1627-1634 (2003)).

Mfge8 is an integrin ligand (Hanayama, R., et al., *Nature* 417, 182-187 (2002)) that is highly expressed in the adipose tissue of mice on a high-fat diet (HFD) (Aoki, N. et al., *Endocrinology* 148, 3850-3862 (2007)). Both the expression of Mfge8 and the integrin receptors for Mfge8 are increased in the adipose tissue of obese humans (Henegar, C. et al., *Genome Biol* 9, R14 (2008)).

DEFINITIONS

An integrin "antagonist" is any agent that competes with an endogenous integrin ligand for available ligand binding sites on an integrin.

A "therapeutic dose," "therapeutic amount," "therapeutically effective amount," or "effective amount" of a molecule antagonist is an amount of the molecule that prevents, alleviates, abates, or reduces the severity of symptoms of a disease or condition to be treated, e.g., a condition involving fatty acid uptake in a patient.

As used herein, the terms "treat" and "prevent" are not intended to be absolute terms. Treatment can refer to any delay in onset, amelioration of symptoms, improvement in patient survival, reduction of tissue damage, etc. Indeed, in some embodiments, treatment according to the invention can result in reversal of the disease. Similarly, prevention can refer to any delay in onset or, depending on context, reduction in severity of symptoms. The effect of treatment can be compared to an individual or pool of individuals not receiving the treatment, or to the same patient, e.g., before treatment.

The term "subject" is used broadly herein to refer to any individual that is considered for treatment. Typically, the subject is a human or some other mammal (e.g., an agricultural animal such as a cattle, pigs, sheep, horses, or goats or a pet such as a dog or a cat).

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$," or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). Various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) *Nature* 348:552). The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochem-* istry 31:1579, Hollinger et al. (1993), *PNAS*. USA 90:6444, Gruber et al. (1994) *J Immunol*. 152:5368, Zhu et al. (1997) *Protein Sci*. 6:781, Hu et al. (1996) *Cancer Res*. 56:3055, Adams et al. (1993) *Cancer Res*. 53:4026, and McCartney, et al. (1995) *Protein Eng*. 8:301.

"Single chain Fv (scFv)" or "single chain antibodies" refers to a protein wherein the $V_H$ and the $V_L$ regions of a scFv antibody comprise a single chain which is folded to create an antigen binding site similar to that found in two chain antibodies. Methods of making scFv antibodies have been described in e.g., Ward et al., *Exp Hematol*. (5):660-4 (1993); and Vaughan et al., *Nat Biotechnol*. 14(3):309-14 (1996). Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser, e.g., 2, 3, 4, 5, or 6 such sequences. However, it is to be appreciated that some amino acid substitutions within the linker can be made. For example, a valine can be substituted for a glycine. Additional peptide linkers and their use are well-known in the art. See, e.g., Huston et al., *Proc. Nat'l Acad. Sci. USA* 8:5879 (1988); Bird et al., *Science* 242:4236 (1988); Glockshuber et al., *Biochemistry* 29:1362 (1990); U.S. Pat. No. 4,946,778, U.S. Pat. No. 5,132,405 and Stemmer et al., *Biotechniques* 14:256-265 (1993).

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

As used herein, "humanized antibody" refers to an immunoglobulin molecule in which CDRs from a donor antibody are grafted onto human framework sequences. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., *Nature* 321:522-525; 1986; Riechmann et al., *Nature* 332:323-327, 1988; Verhoeyen et al., *Science* 239:1534-1536, 1988); Presta, *Curr. Op. Struct. Biol.* 2:593-596, 1992; U.S. Pat. No. 4,816,567), including techniques such as "superhumanizing" antibodies (Tan et al., *J. Immunol*. 169: 1119, 2002) and "resurfacing" (e.g., Staelens et al., *Mol. Immunol*. 43: 1243, 2006; and Roguska et al., *Proc. Natl. Acad. Sci USA* 91: 969, 1994).

As used herein, "V-region" refers to an antibody variable region domain comprising the segments of Framework 1 (F1), Complementarity Determining Region 1 (CDR1), F2, CDR2, and F3, including CDR3 and F4, which segments are added to the V-segment as a consequence of rearrangement of the heavy chain and light chain V-region genes during B-cell differentiation. A "V-segment" as used herein refers to the region of the V-region (heavy or light chain) that is encoded by a V gene. The V-segment of the heavy chain variable region encodes FR1-CDR1-FR2-CDR2 and FR3. For the purposes of this invention, the V-segment of the light chain variable region is defined as extending though FR3 up to CDR3.

As used herein, the term "J-segment" refers to a subsequence of the variable region encoded comprising a C-terminal portion of a CDR3 and the FR4. An endogenous J-segment is encoded by an immunoglobulin J-gene.

As used herein, "complementarity-determining region (CDR)" refers to one of the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, for example, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space. Thus, the position of the CDRs within the V region is relatively conserved between antibodies.

The amino acid sequences and positions of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol* 1997, 273(4)). Definitions of antigen combining sites are also described in the following: Ruiz et al., IMGT, the international ImMunoGeneTics database. *Nucleic Acids Res.*, 28, 219-221 (2000); and Lefranc, M.-P. IMGT, the international ImMunoGeneTics database. *Nucleic Acids Res.* January 1; 29(1): 207-9 (2001); MacCallum et al, Antibody-antigen interactions: Contact analysis and binding site topography, *J. Mol. Biol.*, 262 (5), 732-745 (1996); and Martin et al, *Proc. Natl Acad. Sci. USA*, 86, 9268-9272 (1989); Martin, et al, *Methods Enzymol.*, 203, 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

The phrase "specifically (or significantly or selectively) binds to" when referring to a given protein or peptide, refers to a binding reaction which is determinative of the presence of the protein in the presence of a heterogeneous population of proteins and other biologics. Thus, under designated immunoassay conditions, the specified antibodies or other antagonists bind to a particular protein (e.g., for an αvβ5-specific antibody, an αvβ5 integrin, β5, or portions thereof, or for an αvβ3-specific antibody, an χ, β3, or portions thereof) and do not bind in a significant amount to other proteins present in the sample. Specific binding to an antibody under such conditions may require an antibody that is selected for its specificity for a particular protein. For example, antibodies raised against an αvβ5 integrins or a β5 polypeptide can be further selected to obtain antibodies specifically immunoreactive with that protein and not with other proteins. In some embodiments, the specific antibody will also bind to polymorphic variants of the protein, e.g., proteins at least 80%, 85%, 90%, 95% or 99% identical to a sequence of interest. Generally, an αvβ5-specific antibody or an αvβ3-specific antibody binds to the β component of the integrin as αv has a number of different binding partners. However, as shown in the Example, an antibody specific for αv is effective in blocking fat uptake because the antibody targets both $\alpha_v\beta_3$ and $\alpha_v\beta_5$.

"Specific" or "significant" binding are not intended to be absolute terms. For example, if an antibody does not significantly bind to a particular epitope, it binds with at least 5-fold, 8-fold, 10-fold, 20-fold, 50-fold, 80-fold, or 100-fold reduced affinity as compared to the epitope against which the antibody was raised. Binding affinity can be determined using techniques known in the art, e.g., ELISAs. Affinity can be expressed as dissociation constant (Kd or $K_D$). A relatively higher Kd indicates lower affinity. Thus, for example, the Kd of an αvβ5-specific antibody for αvβ5 will typically be lower by a factor of at least 5, 8, 10, 15, 20, 50, 100, 500, 1000, or more than the Kd of the αvβ5-specific antibody with another protein. One of skill will understand how to design controls to indicate non-specific binding and compare relative binding levels.

A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

An agent that "specifically competes" for binding reduces the specific binding of an antibody to a polypeptide. A first antibody is considered to competitively inhibit binding of a second antibody, if binding of the second antibody to the antigen is reduced by at least 30%, usually at least about 40%, 50%, 60%, 75%, or at least about 90%, in the presence of the first antibody using any of the competitive binding assays known in the art (see, e.g., Harlow and Lane, supra).

The term "equilibrium dissociation constant" or "affinity" abbreviated (Kd or $K_D$), refers to the dissociation rate constant ($k_d$, time$^{-1}$) divided by the association rate constant ($k_a$, time$^{-1}$ M$^{-1}$). Equilibrium dissociation constants can be measured using any known method in the art. Antibodies with high affinity have a monovalent affinity less than about 10 nM, and often less than about 500 pM or about 50 pM as determined by surface plasmon resonance analysis performed at 37° C. In some embodiments, the antibodies of the invention have an affinity (as measured using surface plasmon resonance), of less than 500 pM, typically less than about 100 pM, or even less than 25 pM.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds. For example, the Mfge8 polypeptides described herein can contain one of more non-naturally-occurring amino acid.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "peptidomimetic" and "mimetic" refer to a synthetic chemical compound that has substantially the same structural and functional characteristics of Mfge8 polypeptides or $\alpha_v\beta_5$ and/or $\alpha_v\beta_5$ antagonists. Peptide analogs are commonly used in the pharmaceutical industry as non-peptide drugs with properties analogous to those of the template peptide. These types of non-peptide compound are termed "peptide mimetics" or "peptidomimetics" (see, e.g., Fauchere, *J. Adv. Drug Res.* 15:29 (1986); Veber and Freidinger *TINS* p. 392 (1985); and Evans et al. *J. Med. Chem.* 30:1229 (1987)). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as a naturally occurring αvβ5 ligand, but have one or more peptide linkages optionally replaced by a linkage selected from the group consisting of, e.g., —CH2NH—, —CH2S—, —CH2-CH2—, —CH=CH— (cis and trans), —COCH2—, —CH(OH)CH2—, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As used herein, the terms "nucleic acid" and "polynucleotide" are used interchangeably. Use of the term "polynucleotide" includes oligonucleotides (i.e., short polynucleotides). This term also refers to deoxyribonucleotides, ribonucleotides, and naturally occurring variants, and can also refer to synthetic and/or non-naturally occurring nucleic acids (i.e., comprising nucleic acid analogues or modified backbone residues or linkages), such as, for example and without limitation, phosphorothioates, phosphoramidates, methyl phosphonates, chiral-methyl phosphonates, 2-O-methyl ribonucleotides, peptide-nucleic acids (PNAs), and the like. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (see, e.g., Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the following sequence comparison algorithms or by manual alignment and visual inspection. The invention provides polypeptides that are substantially identical to the polypeptides exemplified herein (e.g., any of SEQ ID NO: 1, 2, 3, 4, 5, or 6). Optionally, the identity exists over a region that is at least about 50 nucleotides in length, or more preferably over a region that is 100 to 500 or 1000 or more nucleotides in length, or the entire length of the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

BRIEF SUMMARY OF THE INVENTION

Methods of reducing fatty acid uptake in an animal are provided. In some embodiments, the method comprises administering an antagonist of integrin αvβ3 or αvβ5 to an animal in an amount sufficient to reduce fatty acid uptake in the animal, thereby reducing fatty acid uptake in the animal. In some embodiments, the animal is a human.

In some embodiments, the antagonist is an antibody In some embodiments, the antibody specifically binds to αvβ3. In some embodiments, the antibody specifically binds to αvβ5 In some embodiments, the antibody is a humanized or chimeric antibody. In some embodiments, the antibody binds the same epitope as ALULA (the antibody produced by the hybridoma deposited under ATCC Deposit No. PTA-5817).

In some embodiments, the animal is obese.

In some embodiments, the animal has reduced insulin sensitivity.

In some embodiments, the animal is insulin resistant.

In some embodiments, the antagonist is administered intravenously, intraperitoneally, subcutaneously, intramuscularly, rectally, or orally.

Also provides is a method of increasing fatty acid uptake and/or gastric motility in an animal. In some embodiments, the method comprises administering a polypeptide comprising (i) Milk Fat Globule Epidermal Growth Factor 8 (Mfge8), or (ii) an integrin-binding portion of Mfge8, to an animal in an amount sufficient to increase fatty acid uptake and/or to gastric motility in the animal.

In some embodiments, the Mfge8 is human Mfge 8 (SEQ ID NO:1) or is at least 80% identical to (i) SEQ ID NO:1 or (ii) an integrin-binding portion of SEQ ID NO:1.

In some embodiments, the animal is human. In some embodiments, the animal (e.g., human) is under two or one years or under six, five, four, three, two, or one months old. In some embodiments, the animal is a premature human infant. In some embodiments, the animal is diabetic or has cystic fibrosis.

In some embodiments, the polypeptide is administered intravenously, intraperitoneally, subcutaneously, intramuscularly, rectally, or orally. In some embodiments, the polypeptide is administered as a component of a composition selected from the group consisting of a powder, a tablet, a capsule, a lozenge, a chewing gum, a food product, a supplemented beverage, or a medical food. In some embodiments, the food product is infant formula.

Also provided is a composition comprising a polypeptide comprising (i) Milk Fat Globule Epidermal Growth Factor 8 (Mfge8), or (ii) an integrin-binding portion of Mfge8. In some embodiments, the Mfge8 is human Mfge 8 (SEQ ID NO:1) or is at least 80% identical to (i) SEQ ID NO:1 or (ii) an integrin-binding portion of SEQ ID NO:1.

In some embodiments, the composition is selected from the group consisting of a powder, a tablet, a capsule, a lozenge, a chewing gum, a food product, a supplemented beverage, or a medical food. In some embodiments, the composition further comprises a bovine milk protein, a soy protein, betalactoglobulin, whey, soybean oil or starch. In some embodiments, said supplemented beverage is a member selected from the group consisting of an infant formula, follow-on formula, toddler's beverage, milk, fruit juice, and fruit-based drink.

DETAILED DESCRIPTION OF THE INVENTION

I. Introduction

Figure 1:
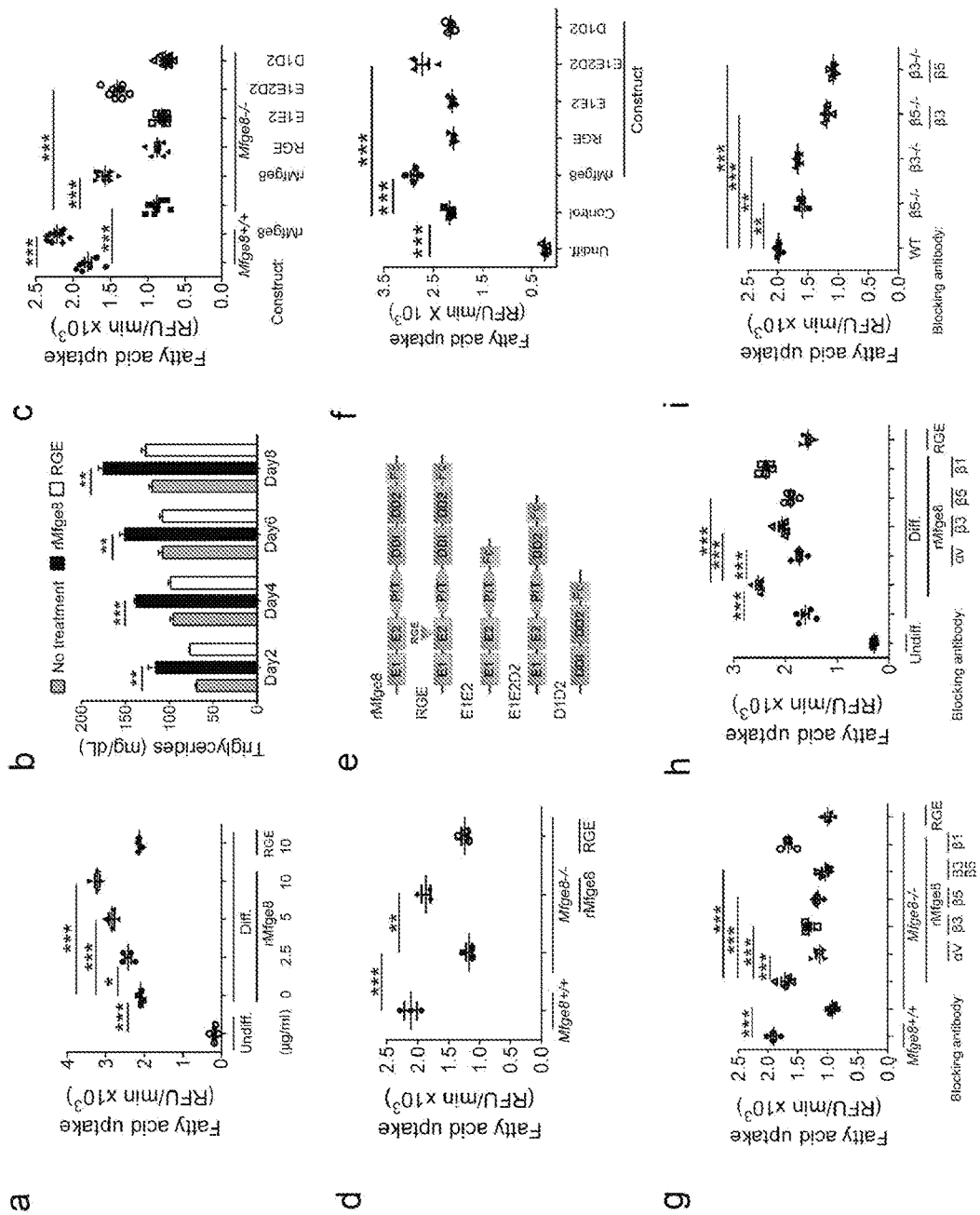
FIGS. 1A-1I. Mfge8 mediates fatty acid uptake in adipocytes. (A) Fatty acid uptake in undifferentiated 3T3-L1 fibroblasts and differentiated 3T3-L1 adipocytes treated with the rMfge8 or RGE construct. N=4. (B) 3T3-L1 adipocyte triglyceride content after treatment with the rMfge8 or RGE construct (10 μg/ml). N=3. (C-F) Fatty acid uptake in Mfge8−/− primary adipocytes (C, N=7-9), differentiated primary Mfge8−/− adipocyte progenitors cells (D, N=3), and 3T3-L1 adipocytes (F, N=4) after incubation with mutated Mfge8 constructs (E). (G,H) Effect of integrin blocking antibodies on fatty acid uptake in Mfge8−/− adipocytes treated with rMfge8 (G, N=3-4) and in 3T3-L1 adipocytes (H, N=5). (I) Fatty acid uptake in β5−/− and β3−/− primary adipocytes with and without the addition of integrin blocking antibodies. N=4. *P<0.01, P<0.001, *P<0.0001. Data are expressed as mean±s.e.m. Each replicate represents an independent experiment.

Surprisingly, it has been discovered that Milk Fat Globule Epidermal Growth Factor 8 (Mfge8) stimulates fatty acid uptake. In view of this discovery, Mfge8 and analogs thereof will be useful in stimulating fatty uptake in animals (including but not limited to humans) in need thereof. Individuals who will benefit from stimulated fatty acid uptake include but are not limited to premature infants, individuals with excessive gastric emptying, diabetics and those with cystic fibrosis.

Conversely, blocking Mfge8 binding to integrin receptors $\alpha_v\beta_3$ or $\alpha_v\beta_5$ inhibits fatty acid uptake. Blocking fatty acid uptake is useful, for example, in weight loss. Accordingly, administration of antagonists of $\alpha_v\beta_3$ or $\alpha_v\beta_5$ is useful for inducing weight loss in animals (e.g., humans), and is particularly useful for obese individuals. In addition, administration of antagonists of $\alpha_v\beta_3$ or $\alpha_v\beta_5$ can also enhance insulin sensitivity and can be used to treat individuals with reduced insulin sensitivity or insulin resistance.

II. Increasing Mfge8 Signaling

As noted above, it has been discovered that Mfge8 increases fatty acid uptake in various organs. Accordingly, in some embodiments, a polypeptide comprising Mfge8, or a substantially identical sequence thereof, or an integrin-binding fragment thereof is administered to an animal, thereby increasing fatty acid uptake in the animal. In some embodiments, a Mfge8 polypeptide as described herein is administered to an individual suffering from fat malabsorption.

In some aspects, an individual in need of increased fatty acid uptake/adsorption is treated with a Mfge8 polypeptide as described herein. In some aspects, the individual has excess gastric emptying or otherwise has difficulty extracting nutrients from food. In some embodiments, the individual is a premature infant (e.g., born prior to completion of gestation) or is otherwise nursing. In some embodiments, the individual is less than 1 or 2 years old. In some embodiments, the individual is less than 6, 5, 4, 3, 2, or 1 month old. Additional examples of individuals (e.g., suffering from fat malabsorption) to which Mfge8 polypeptides can be administered include individuals having cystic fibrosis, individuals who undergo gastric bypass surgery, individuals with a decrease in the small intestine lymphatics, individuals having altered duodenal pH (Zollinger-Ellison syndrome), individuals having improper emulsification after certain types of gastrectomy, individuals having rapid transit dumping syndrome, rapid transit dumping syndrome having acute abnormality in the intestinal lining, e.g., because of infections, antibiotics or alcohol abuse, rapid transit dumping syndrome having small bowel syndrome, rapid transit dumping syndrome having presence of a chronic abnormal intestinal lining, e.g., as a result of conditions such as Crohn's disease or Celiac disease, rapid transit dumping syndrome having improper intestinal environments, e.g., because of bacterial overgrowth or the presence of parasites in the digestive system, rapid transit dumping syndrome having inadequate gastric mixing, e.g., due to factors such as a fistula in the gastric environment or after a gastrostomy, rapid transit dumping syndrome having impaired movement of the enzymes in the body, individuals having intestinal lymphangiectasia, individuals having Whipple's Disease, rapid transit dumping syndrome having irritable bowel syndrome and/or inflammatory bowel disease, individuals having cancer (e.g., advanced cancer such as Stage III or Stage IV). A Mfge8 polypeptide as described herein is administered to an individual having pancreatic and biliary dysfunction, including but not limited to individuals having chronic pancreatitis, obstruction in the pancreatic duct, pancreatic cancer, resection of the pancreas, Shwachmann-Diamond syndrome, Johnson-Blizzard syndrome, or Pearson syndrome.

A variety of polypeptides can be used according to the methods for increasing fatty acid uptake. In some embodiments, full-length native (or variants thereof) Mfge8 protein amino acid sequences are used in the methods described herein. In some embodiments, the polypeptides comprise a fragment (not the full-length native sequence) of the Mfge8 sequence, or a variant thereof, that retains the ability to bind to integrin $\alpha_v\beta_3$ or $\alpha_v\beta_5$. Binding of Mfge8 to the integrin receptors is through the RGD motif and thus in some embodiments the Mfge8 fragment will comprise at least RGD, and in some aspects at least 2, 4, 5, 10, or 20 native amino acids of Mfge8 on either side of the RGD motif. Thus, in some embodiments, the polypeptides comprise at least a fragment (e.g., at least 20, 40, 50, 100, 150, 200, 250 contiguous amino acids) of the native Mfge8 protein. The inventors have found that the sequence set forth in SEQ ID NO:4, which is a mouse Mfge8 sequence lacking the second discoidan domain but including all other native sequence, remains active. The full length mouse Mfge8 sequence is depicted in SEQ ID NO:3.

In some aspects the Mfge8 protein or fragment thereof will be derived from the animal species to be treated. Thus, for example, if a human is to be treated, a human Mfge8 (e.g., SEQ ID NO:1) or fragment thereof is administered. As another example, if cattle are to be treated, a bovine Mfge8 (e.g., SEQ ID NO:5) or a fragment or substantially identical polypeptide thereof is used.

While not required, in some embodiments, the Mfge8 polypeptides will include non-native Mfge8 protein flanking sequences. For example, a full-length Mge8 or an RGD-containing fragment of Mfge8 can be fused to one or more heterologous amino acids to form a fusion protein. Fusion partner sequences can include, but are not limited to, amino acid tags, non-L (e.g., D-) amino acids or other amino acid mimetics to extend in vivo half-life and/or protease resistance, targeting sequences or other sequences.

In some embodiments, the MFGE8 polypeptides will comprise at least one non-naturally encoded amino acid. Methods of making and introducing a non-naturally-occurring amino acid into a protein are known. See, e.g., U.S. Pat. Nos. 7,083,970; and 7,524,647. The general principles for the production of orthogonal translation systems that are suitable for making proteins that comprise one or more desired unnatural amino acid are known in the art, as are the general methods for producing orthogonal translation systems. For example, see International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; WO 2005/007624, filed Jul. 7, 2004; WO 2006/110182, filed Oct. 27, 2005, entitled "ORTHOGONAL TRANSLATION COMPONENTS FOR THE VIVO INCORPORATION OF UNNATURAL AMINO ACIDS" and WO 2007/103490, filed Mar. 7, 2007, entitled "SYSTEMS FOR THE EXPRESSION OF ORTHOGONAL TRANSLATION COMPONENTS IN EUBACTERIAL HOST CELLS." Each of these applications is incorporated herein by reference in its entirety. For discussion of orthogonal translation systems that incorporate unnatural amino acids, and methods for their production and use, see also, Wang and Schultz, (2005) "Expanding the Genetic Code." Angewandte Chemie Int Ed 44: 34-66; Xie and Schultz, (2005) "An Expanding Genetic Code." Methods 36: 227-238; Xie and Schultz, (2005) "Adding Amino Acids to the Genetic Repertoire." Curr Opinion in Chemical Biology 9: 548-554; and Wang, et al., (2006) "Expanding the Genetic Code." Annu Rev Biophys Biomol Struct 35: 225-249; Deiters, et al, (2005) "In vivo incorporation of an alkyne into proteins in *Escherichia coli*." Bioorganic & Medicinal Chemistry Letters 15:1521-1524; Chin, et al., (2002) "Addition of p-Azido-L-phenylalanine to the Genetic Code of *Escherichia coli*." J Am Chem Soc 124: 9026-9027; and International Publication No. WO2006/034332, filed on Sep. 20, 2005, the contents of each of which are incorporated by reference in their entirety. Additional details are found in U.S. Pat. No. 7,045,337; No. 7,083,970; No. 7,238,510; No. 7,129,333; No. 7,262,040; No. 7,183,082; No. 7,199,222; and No. 7,217,809.

A "non-naturally encoded amino acid" refers to an amino acid that is not one of the common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

A non-naturally encoded amino acid is typically any structure having any substituent side chain other than one used in the twenty natural amino acids. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Another type of modification that can optionally be introduced into the MFGE8 polypeptide (e.g., within the polypeptide chain or at either the N- or C-terminal), e.g., to extend in vivo half-life, is PEGylation or incorporation of long-chain polyethylene glycol polymers (PEG). Introduction of PEG or long chain polymers of PEG increases the effective molecular weight of the present polypeptides, for example, to prevent rapid filtration into the urine. In some embodiments, a Lysine residue in the MFGE8 sequence is conjugated to PEG directly or through a linker. Such linker can be, for example, a Glu residue or an acyl residue containing a thiol functional group for linkage to the appropriately modified PEG chain. An alternative method for introducing a PEG chain is to first introduce a Cys residue at the C-terminus or at solvent exposed residues such as replacements for Arg or Lys residues. This Cys residue is then site-specifically attached to a PEG chain containing, for example, a maleimide function. Methods for incorporating PEG or long chain polymers of PEG are well known in the art (described, for example, in Veronese, F. M., et al., *Drug Disc. Today* 10: 1451-8 (2005); Greenwald, R. B., et al., *Adv. Drug Deliv. Rev.* 55: 217-50 (2003); Roberts, M. J., et al., *Adv. Drug Deliv. Rev.*, 54: 459-76 (2002)), the contents of which is incorporated herein by reference. Other methods of polymer conjugations known in the art can also be used in the present invention. In some embodiments, poly(2-methacryloyloxyethyl phosphorylcholine) (PMPC) is introduced as a polymer conjugate with the MFGE8 proteins of the invention (see, e.g., WO2008/098930; Lewis, et al., *Biocon-jug Chem.*, 19: 2144-55 (2008)). In some embodiments, a phosphorylcholine-containing polymer conjugate with the MFGE8 proteins can be used in the present invention. Other biocompatible polymer conjugates can also be utilized.

A more recently reported alternative approach for incorporating PEG or PEG polymers through incorporation of non-natural amino acids (as described above) can be performed with the present Mfge8 polypeptides. This approach utilizes an evolved tRNA/tRNA synthetase pair and is coded in the expression plasmid by the amber suppressor codon (Deiters, A, et al. (2004). *Bio-org. Med. Chem. Lett.* 14, 5743-5). For example, p-azidophenylalanine can be incorporated into the present polypeptides and then reacted with a PEG polymer having an acetylene moiety in the presence of a reducing agent and copper ions to facilitate an organic reaction known as "Huisgen [3+2]cycloaddition."

In certain embodiments, specific mutations of the MFGE8 proteins are contemplated so as to alter the glycosylation of the polypeptide. Such mutations may be selected so as to introduce or eliminate one or more glycosylation sites, including but not limited to, O-linked or N-linked glycosylation sites. In certain embodiments, the MFGE8 proteins have glycosylation sites and patterns unaltered relative to the naturally-occurring MFGE8 proteins. In certain embodiments, a variant of MFGE8 proteins includes a glycosylation variant wherein the number and/or type of glycosylation sites have been altered relative to the naturally-occurring MFGE8 proteins. In certain embodiments, a variant of a polypeptide comprises a greater or a lesser number of N-linked glycosylation sites relative to a native polypeptide. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. In certain embodiments, a rearrangement of N-linked carbohydrate chains is provided, wherein one or more N-linked glycosylation sites (typically those that are naturally occurring) are eliminated and one or more new N-linked sites are created.

Exemplary MFGE8 proteins variants include cysteine variants wherein one or more cysteine residues are deleted from or substituted for another amino acid (e.g., serine) relative to the amino acid sequence of the naturally-occurring MFGE8 proteins. In certain embodiments, cysteine variants may be useful when MFGE8 proteins must be refolded into a biologically active conformation such as after the isolation of insoluble inclusion bodies. In certain embodiments, cysteine variants have fewer cysteine residues than the native polypeptide. In certain embodiments, cysteine variants have an even number of cysteine residues to minimize interactions resulting from unpaired cysteines.

In some embodiments, functional variants or modified forms of the MFGE8 proteins include fusion proteins of an MFGE8 protein of the invention and one or more fusion domains. Well known examples of fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QLAexpress™ system (Qiagen) useful with fusion partners (e.g., $His_6$; SEQ ID NO:7). As another example, a fusion domain may be selected so as to facilitate detection of the MFGE8 proteins. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, an MFGE8 protein is fused with a domain that stabilizes the MFGE8 protein in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins.

Likewise, fusions to human serum albumin can confer desirable properties. Other types of fusion domains that may be selected include multimerizing (e.g., dimerizing, tetramerizing) domains and functional domains (that confer an additional biological function, as desired).

It is contemplated that the polypeptides, compositions, and methods of the present invention may be used to treat a mammal. As used herein a "mammal" to any mammal classified as a mammal, including humans, domestic and farm animals, and zoo, sports or pet animals, such as cattle (e.g. cows), horses, dogs, sheep, pigs, rabbits, goats, cats, etc. All embodiments described herein not specifically referring to another species should be understood to specifically apply to humans as well as more generally to mammals.

The dose of a compound of the present invention for treating the above-mentioned diseases or disorders varies depending upon the manner of administration, the age and the body weight of the subject, and the condition of the subject to be treated, and ultimately will be decided by the attending physician or veterinarian. Such an amount of the compound as determined by the attending physician or veterinarian is referred to herein as an "effective amount."

Formulations suitable for administration include exipients, including but not limited to, aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In some embodiments, the Mfge8 polypeptides are formulated in micelles or liposomes.

The dose administered to a patient, in the context of the present invention should be sufficient to effect a beneficial response in the subject over time. The dose will be determined by the efficacy of the particular protein employed and the condition of the subject, as well as the body weight or surface area of the area to be treated. The size of the dose also will be determined by the existence, nature, and extent of any adverse side-effects that accompany the administration of a particular protein or vector in a particular subject. Administration can be accomplished via single or divided doses.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, rectally, nasally, topically, intravenously, intraperitoneally, or intrathecally. The formulations of polypeptides can be presented in unit-dose or multi-dose sealed containers, such as ampoules and vials. Solutions and suspensions can be prepared from sterile powders, granules, and tablets of the kind previously described. The modulators can also be administered as part a of prepared food or drug.

In general, any food or beverage that can be consumed by human infants or adults or animals may be used to make formulations containing the Mfge8 polypeptides described herein. Exemplary foods include those with a semi-liquid consistency to allow easy and uniform dispersal of the compositions. However, other consistencies (e.g., powders, liquids, etc.) can also be used without limitation. Accordingly, such food items include, without limitation, dairy-based products such as cheese, cottage cheese, yogurt, and ice cream. Processed fruits and vegetables, including those targeted for infants/toddlers, such as apple sauce or strained vegetables (e.g., peas and carrots, etc.), are also suitable for use in combination with the prebiotic and synbiotic compositions of the present invention. Both infant cereals such as rice- or oat-based cereals and adult cereals such as Musilix are also suitable for use in combination with the oligosaccharides of the present invention. In addition to foods targeted for human consumption, animal feeds may also be supplemented with the Mfge8 polypeptides as described herein.

Alternatively, the Mfge8 polypeptide compositions can be used to supplement a beverage. Examples of such beverages include, without limitation, infant formula, follow-on formula, toddler's beverage, milk, fermented milk, fruit juice, fruit-based drinks, and sports drinks Many infant and toddler formulas are known in the art and are commercially available, including, for example, Carnation Good Start (Nestle Nutrition Division; Glendale, Calif.) and Nutrish A/B produced by Mayfield Dairy Farms (Athens, Tenn.). Other examples of infant or baby formula include those disclosed in U.S. Pat. No. 5,902,617. Other beneficial formulations of the compositions of the present invention include the supplementation of animal milks, such as cow's milk.

Alternatively, the prebiotic and probiotic compositions of the present invention can be formulated into pills or tablets or encapsulated in capsules, such as gelatin capsules. Tablet forms can optionally include, for example, one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge or candy forms can comprise the compositions in a flavor, e.g., sucrose, as well as pastilles comprising the compositions in an inert base, such as gelatin and glycerin or sucrose and acacia emulsions, gels, and the like containing, in addition to the active ingredient, carriers known in the art. The Mfge8 polypeptide formulations may also contain conventional food supplement fillers and extenders such as, for example, rice flour.

In some embodiments, the Mfge8 polypeptide composition will further comprise a non-human protein, non-human lipid, non-human carbohydrate, or other non-human component. For example, in some embodiments, the compositions of the invention comprise a bovine (or other non-human) milk protein, a soy protein, a rice protein, betalactoglobulin, whey, soybean oil or starch. In some embodiments, the prebiotic or synbiotic composition will further comprise a non-bovine protein, non-bovine lipid, non-bovine carbohydrate, or other non-bovine component.

III. Inhibiting MFGE8 Signaling

Mfge8 is a ligand for both $\alpha_v\beta_3$ and $\alpha_v\beta_5$ integrins. As demonstrated below in Examples 1 and 2, administration of an antagonist antibody that binds the $\alpha v$ integrin subunit completely inhibited fat uptake in an animal and administration of an antibody specific for $\alpha_v\beta_3$ or administration of an antibody specific for $\alpha_v\beta_5$ partially decreases fat absorption. Accordingly, antagonizing the $\alpha_v\beta_3$ and/or $\alpha_v\beta_5$ integrin receptors is effective to reduce fat uptake and optionally for weight reduction in an individual.

Co-administration of antagonists of $\alpha_v\beta_3$ and/or $\alpha_v\beta_5$ integrin receptors and insulin can be used to treat individuals with reduced insulin sensitivity. In particular, pretreatment with antagonists of $\alpha_v\beta_3$ and/or $\alpha_v\beta_5$ integrin receptors prior to insulin injection can significantly lower serum glucose levels, as compared to injection of insulin alone.

Exemplary antagonists can be, for example, antagonist antibodies, e.g., antagonists antibodies that specifically bind to $\alpha_v\beta_3$ and/or $\alpha_v\beta_5$ integrin receptors. An exemplary $\alpha_v\beta_5$ antibody is "ALULA" (the antibody produced by the hybridoma deposited under ATCC Deposit No. PTA-5817, made Feb. 13, 2004, at the ATCC, 10801 University Blvd. Manassas, Va. 20110-2209). Alternatively, the $\alpha_v\beta_3$ and/or $\alpha_v\beta_5$ integrin receptor antagonists can be small molecules. See, e.g., PCT WO 2003/059872. In some embodiments, the antagonists are RGD-containing peptides or cyclic peptides. Examples of such peptides include, but are not limited to those described in Belvisi, L., et al., *Mol Cancer Ther* 4(11): (November 2005). Some antagonists are reviewed in Hsu, A R, et al., *Recent Pat Anticancer Drug Discov.* 2(2):143-58 (2007).

In some embodiments, the $\alpha_v\beta_3$ and/or $\alpha_v\beta_5$ integrin receptor antagonists are administered to an individual that is overweight overweight (e.g., body mass index (BMI) greater or equal to 25 kg/m$^2$) or is obese. In some embodiments, the $\alpha_v\beta_3$ and/or $\alpha_v\beta_5$ integrin receptor antagonists are administered to an individual with high (i.e., above average) level of fatty acids and triglycerides, and an individual with hyperlipidemia or dyslipidemia (e.g., an individual having cirrhosis or liver damage, hypothyroidism (underactive thyroid), nephrotic syndrome, a kidney disorder, or diabetes. In some embodiments, the $\alpha_v\beta_3$ and/or $\alpha_v\beta_5$ integrin receptor antagonists are administered to a pregnant individual or an individual with elevated levels of female hormones. In some embodiments, the $\alpha_v\beta_3$ and/or $\alpha_v\beta_5$ integrin receptor antagonists are administered to an individual with an elevated risk cardiovascular disease or stroke. In some embodiments, the $\alpha_v\beta_3$ and/or $\alpha_v\beta_5$ integrin receptor antagonists are administered to an individual with reduced insulin sensitivity or insulin resistance.

The $\alpha_v\beta_3$ and/or $\alpha_v\beta_5$ integrin receptor antagonists can be formulated and administered as described above with regard to the Mfge8 polypeptides. For example, formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, rectally, nasally, topically, intravenously, intraperitoneally, or intrathecally. The formulations of polypeptides can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

EXAMPLES

Example 1: Mfge8 and Regulating Fat Storage and Lipid Homeostasis

Fatty acids are integral mediators of energy storage, membrane formation, and cell signaling. The pathways that orchestrate uptake of fatty acids remain incompletely understood. Expression of the integrin ligand Mfge8 is increased in human obesity and in mice on a high-fat diet (HFD). The role of Mfge8 in obesity is unknown. We show here that Mfge8 promotes the development of obesity by facilitating cellular uptake of fatty acids. Mfge8 deficient (Mfge8−/−) mice absorb less dietary triglycerides and are protected from weight gain, steatohepatitis and obesity-associated insulin resistance on a HFD. Mfge8−/− cells have impaired fatty acid uptake in vitro. Mfge8 coordinates fatty acid uptake through $\alpha_v\beta_3$ and $\alpha_v\beta_5$ integrin-dependent phosphorylation of AKT by PI3 kinase and mTOR complex 2 leading to translocation of CD36 and FATP1 from cytosolic stores to the cell surface. Collectively, our results implicate a central role for Mfge8 in regulating fat storage and lipid homeostasis.

Results

Mfge8 Increases 3T3-L1 Adipocyte Fatty Acid Uptake and Triglyceride Storage

To evaluate the effect of Mfge8 on fatty acid uptake, we quantified the effect of recombinant Mfge8 (rMfge8) on uptake of a BODIPY fatty acid analog (Liao, J. et al., *J Lipid Res* 46, 597-602 (2005)) by 3T3-L1 adipocytes. rMfge8 significantly increased fatty acid uptake in a dose-dependent fashion (FIG. 1A), while a recombinant construct with a point mutation changing the integrin-binding RGD sequence of Mfge8 to RGE (RGE) had no effect (FIG. 1A). 3T3-L1 cells treated with rMfge8, but not RGE, had significantly greater triglyceride content 2, 4, 6, and 8 days after treatment (FIG. 1B). These data indicate that Mfge8 increases fatty acid uptake and triglyceride stores in 3T3-L1 adipocytes through an integrin-dependent pathway.

Mfge8−/− Adipocytes have Impaired Fatty Acid Uptake that is Rescued with rMfge8.

We next evaluated whether fatty acid uptake was impaired in adipocytes from Mfge8−/− mice. Mfge8−/− primary adipocytes isolated from epididymal white adipose tissue (eWAT) and differentiated adipocyte progenitors isolated from subcutaneous white adipose tissue had significantly impaired fatty acid uptake (FIGS. 1C,D). rMfge8 rescued the decrease in fatty acid uptake in Mfge8−/− adipocytes and significantly increased WT fatty acid uptake (FIGS. 1C,D). In addition to an intact integrin-binding motif, the effect of recombinant protein required at least one of the discoidin domains of Mfge8 (FIGS. 1C,E,F). Treatment of 323-L1 adipocytes with cycloRGD did not induce an increase in AKT phosphorylation or fatty acid uptake.

The Effect of Mfge8 on Fatty Acid Uptake is Mediated Through the $\alpha_v\beta_5$ and $\alpha_v\beta_3$ Integrins.

Mfge8 is a ligand for the $\alpha v\beta 3$ and $\alpha v\beta 5$ integrins (Hanayama, R. et al., *Nature* 417, 182-187 (2002)). To determine whether Mfge8 mediated fatty acid uptake through these integrins, we evaluated the effects of integrin-blocking antibodies on the ability of rMfge8 to rescue impaired fatty acid uptake in Mfge8−/− adipocytes (FIG. 1G) and increase fatty acid uptake in 3T3-L1 adipocytes (FIG. 1H). Blocking antibody to the $\alpha v$ integrin subunit or both the $\beta 3$ and $\beta 5$ subunits completely inhibited and blocking antibodies to the $\beta 5$ or the $\beta 3$ integrin subunits partially inhibited the increase in fatty acid uptake induced by rMfge8 (FIGS. 1G,H). During 3T3-L1 differentiation from fibroblasts into adipocytes, Mfge8 expression increased, while expression of $\alpha v$, $\beta 3$ and $\beta 5$ integrin subunits was stably persistent. $\beta 5$−/− and $\beta 3$−/− adipocytes had impaired fatty acid uptake which was further reduced with the addition of blocking antibody to the $\beta 3$ integrin subunit in $\beta 5$−/− adipocytes and vice versa. These data indicate that the $\alpha v\beta 3$ and $\alpha v\beta 5$ integrins mediate the effect of Mfge8 on fatty acid uptake.

Mfge8 Regulates Hepatic and Cardiac Fatty Acid Uptake

To determine whether the effect of Mfge8 on fatty acid uptake could be generalized to other tissues, we evaluated fatty acid uptake in hepatocytes and cardiac myocytes.

Figure 2:
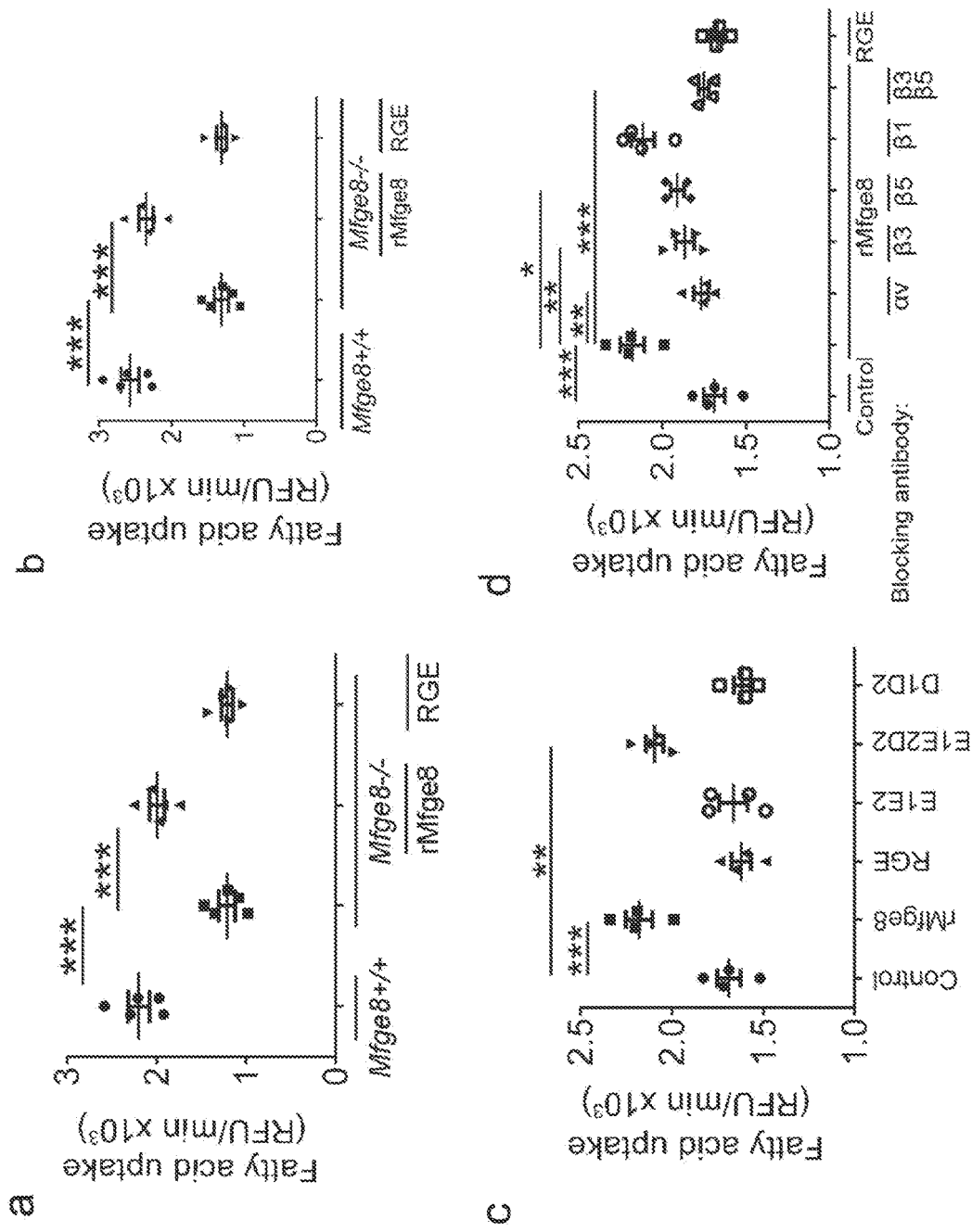
FIGS. 2A-2D. Mfge8 mediates fatty acid uptake in hepatocytes and cardiac myocytes. (A) Fatty acid uptake in primary Mfge8+/+ and Mfge8−/− hepatocytes, and Mfge8−/− hepatocytes treated with rMfge8 or RGE. N=6. (B) Fatty acid uptake in primary Mfge8+/+ and Mfge8−/− cardiac myocytes and Mfge8−/− cardiac myocytes treated with rMfge8 or RGE. N=6. (C) The effect of mutated Mfge8 constructs on fatty acid uptake by HepG2 cells. N=4. (D) The effect of integrin blocking antibodies (20 μg/mL) on fatty acid uptake in HepG2 cells treated with rMfge8. *P<0.01, P<0.001, *P<0.0001. Data are expressed as mean±s.e.m. Each replicate represents an independent experiment.

Mfge8−/− hepatocytes and cardiac myocytes had impaired fatty acid uptake that was rescued with rMfge8 (FIGS. 2A,B). rMfge8 also increased fatty acid uptake in HepG2 cells, a human hepatocellular carcinoma cell line, in an integrin binding and discoidin domain dependent manner (FIGS. 2C,D).

Mfge8 Mediates Fatty Acid Uptake and Absorption of Dietary Triglycerides in the Gastrointestinal Tract.

Figure 3:
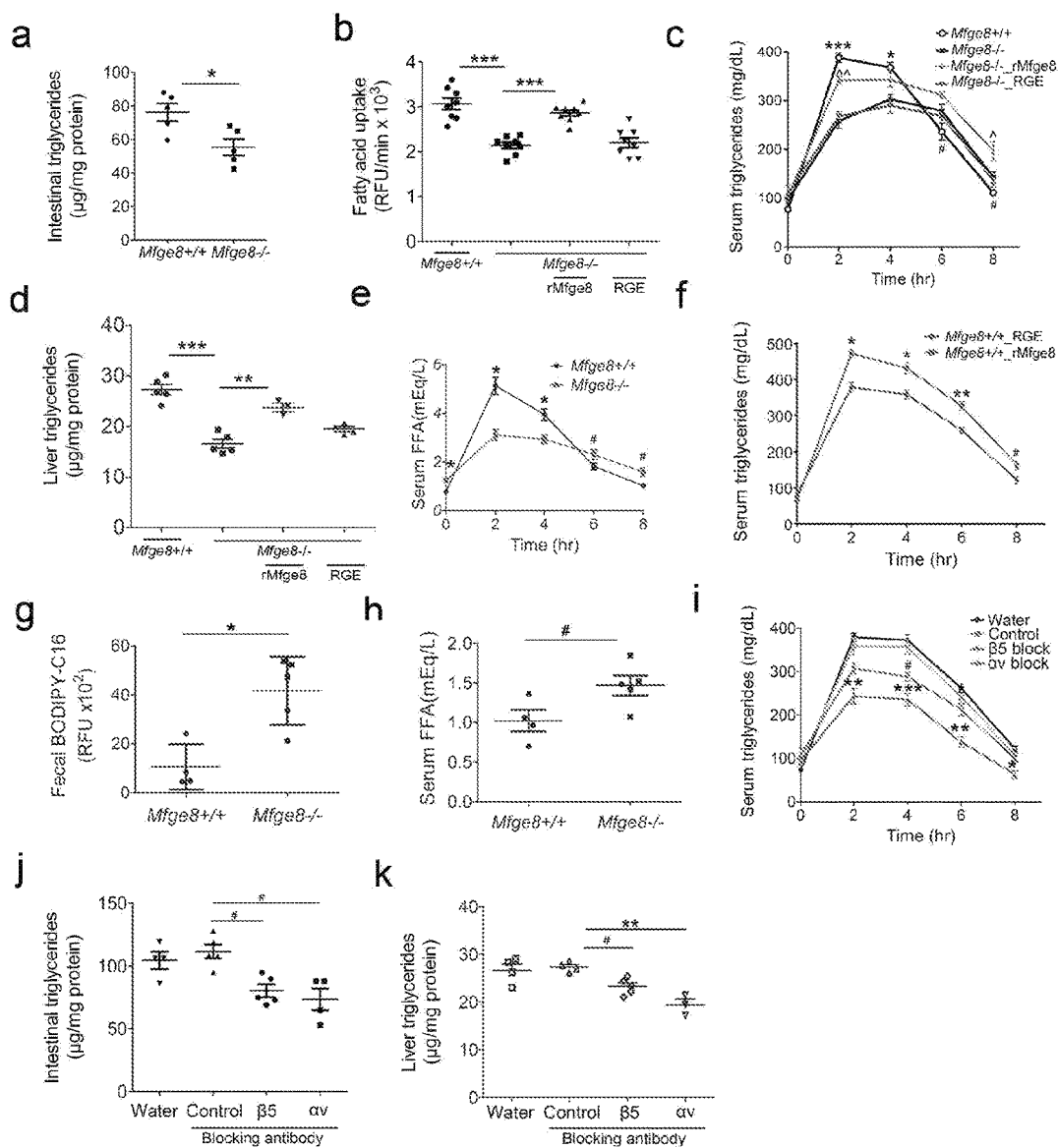
FIGS. 3A-3K. Mfge8 mediates fatty acid uptake in the intestinal tract. (A) Triglyceride content of the small intestine in mice fasted for 8 hours. N=5. (B) Fatty acid uptake in primary Mfge8+/+ and Mfge8−/− enterocytes, and Mfge8−/− enterocytes treated with rMfge8 or RGE. N=8. (C) Serum triglycerides after oral gavage of Mfge8+/+ and Mfge8−/− mice with olive oil and Mfge8−/− mice with olive oil mixed with rMfge8 or RGE construct. N=3-5, *P<0.01, ***P<0.0001 when comparing Mfge8−/− with Mfge8+/+ mice, ^^P<0.01, ^P<0.05 when comparing Mfge8−/− mice with Mfge8−/− treated with rMfge8, #P<0.01 when comparing Mfge8+/+ mice with Mfge8−/− treated with rMfge8. (D) Liver triglyceride levels 8 hours after olive oil gavage as described for FIG. 3C. N=3-5. (E) Serum free fatty acid levels in Mfge8+/+ and Mfge8−/− mice after olive oil gavage, N=4-5. (F) Effect of rMfge8 or RGE construct on serum triglycerides after olive oil gavage in Mfge8+/+ mice. N=4-5. (G) Fecal fatty acid levels in Mfge8+/+ and Mfge8−/− mice after gavage with BODIPY fatty acid analog. N=4-5. (H) Serum free fatty acid levels in Mfge8+/+ and Mfge8−/− mice after a 24 hour fast, N=4-5. (I-K) Effect of oral administration of integrin blocking antibodies prior to olive oil gavage on serum triglycerides levels (G, *P<0.01, P<0.001, *P<0.0001, when comparing αv antibody with control antibody, #P<0.01 when comparing 135 antibody with control antibody), and on small intestine (FIG. 3H) and liver triglyceride content (FIG. 3I) in Mfge8+/+ mice. N=4-5 for panels, I-K. #P<0.05, *P<0.01, P<0.001, *P<0.0001 where not previously specified. Data are expressed as mean±s.e.m. Each in vivo experiment was performed once. For in vitro experiments in panel B, each replicate represents an independent experiment.

The high expression of Mfge8 in breast milk (Newburg, D. S. et al., *Lancet* 351, 1160-1164 (1998)) led us to investigate a role for Mfge8 in intestinal fat absorption. We found significantly reduced small intestinal triglyceride content in Mfge8−/− mice (FIG. 3A) and reduced in vitro fatty acid uptake by Mfge8−/− primary enterocytes (FIG. 3B). Mfge8−/− mice had significantly lower serum triglyceride levels after olive oil gavage. Adding rMfge8, but not RGE, to olive oil significantly raised serum triglyceride levels (FIG. 3C). Liver triglyceride levels after gavage were significantly lower in Mfge8−/− mice and increased significantly with rMfge8 treatment (FIG. 3D). Serum fatty acid levels after olive oil gavage were also lower in Mfge8−/− mice (FIG. 3E). rMfge8 significantly increased WT serum triglyceride levels after olive oil gavage (FIG. 3F). There was no difference in serum glucose levels after glucose gavage when comparing Mfge8−/− and WT mice or in glucose uptake by 3T3-L1 adipocytes treated with rMfge8. To prove that Mfge8 deficiency led to fatty acid malabsorption, we administered a gavage of BODIPY fatty acid analog and measured fecal BODIPY content. Mfge8−/− mice had significantly greater fecal BODIPY levels (FIG. 3G). To separate the effects of impaired enteral absorption of fatty acids from impaired peripheral uptake of fatty acids on serum fatty acid levels, we measured serum free fatty acids after fasting mice for 24 hours. Mfge8−/− mice had significantly higher serum free fatty acids (FIG. 3H) indicating a defect in peripheral uptake of fatty acids after starvation-induced lipolysis.

Figure 7:
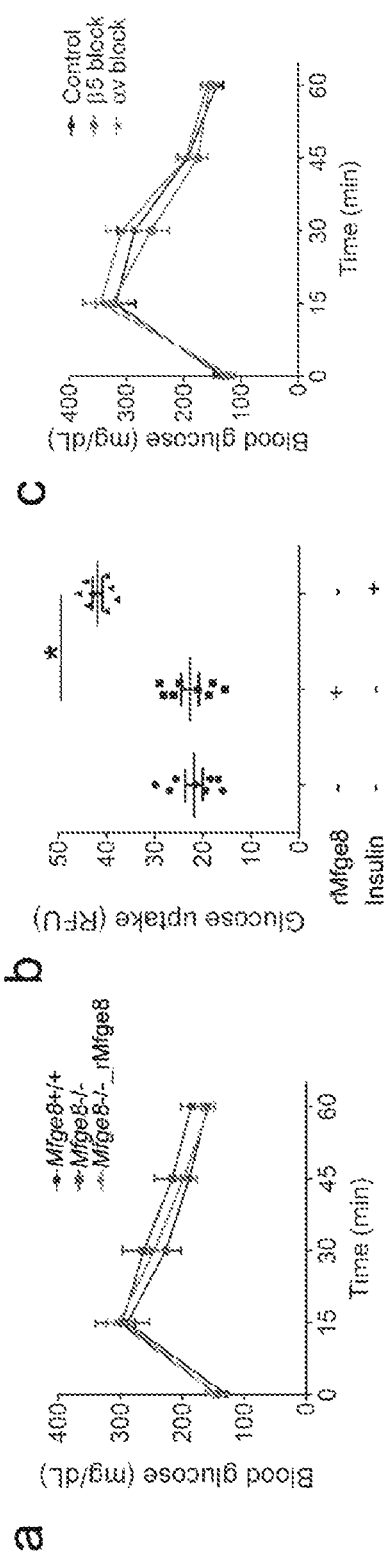
FIGS. 7A-7C. Mfge8 does not regulate glucose homeostasis. (A) Serum glucose levels after gavage with a glucose bolus in Mfge8+/+ and Mfge8−/− mice and gavage of glucose mixed with rMfge8 in Mfge8−/− mice. N=4-5. (B) Effect of rMfge8 and insulin on glucose uptake in 3T3-L1 adipocytes. N=7-8, each replicate represents an independent experiment. (C) Effect of integrin blocking antibodies or control antibody on glucose adsorption by Mfge8+/+ mice after glucose gavage. N=4-5. Data are expressed as mean±s.e.m. Each replicate represents an independent experiment. *P<0.01.
Figure 8:
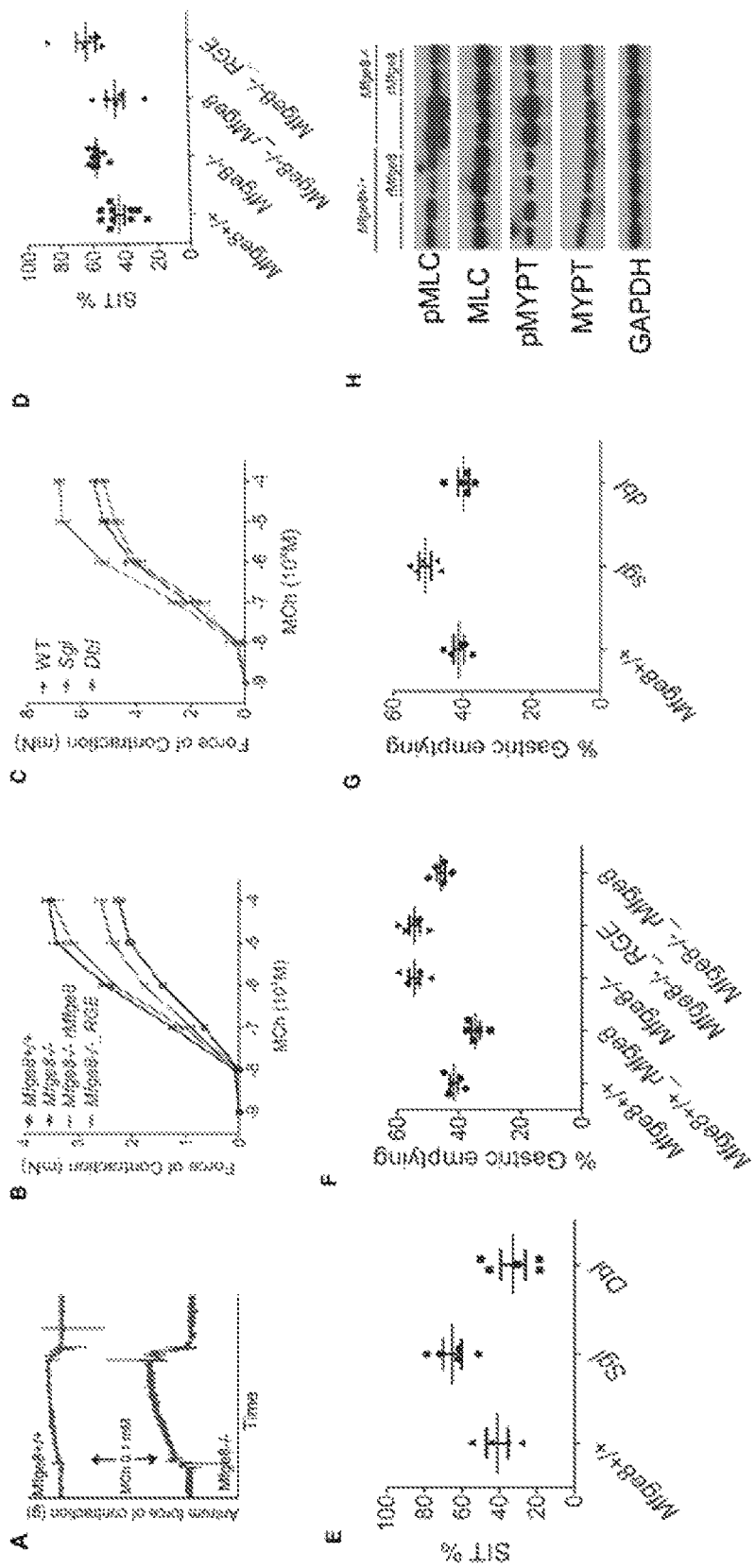
FIGS. 8A-8H demonstrates an effect of Mfge8 on gastric motility. (A,B) Smooth muscle strips from stomach of Mfge KO (knockout) mice have stronger contraction and thus can be rescued by addition of rMfge8. (C) Represents the same experiment as FIGS. 13A and B but using mice that only express Mfge8 in smooth muscle (dbl-means transgenic mice in the Mfge8 KO background that express Mfge8 in smooth muscle), have no Mfge8 (single-sgl), or are wild type. (D, E) Increased small intestinal transit time with rescue groups as above in Mfge8 KO mice. (F, G) More rapid gastric emptying in Mfge KO with same rescue as above. (H) Increased phosphorylation of MLCP meaning enhanced calcium sensitivity in Mfge8 KO mice.

We next evaluated the ability of enteral integrin blockade to prevent fat absorption in WT mice. The administration of αv-blocking or β5-blocking antibody by gavage 30 minutes prior to receiving an olive oil bolus significantly reduced serum triglyceride levels, enterocyte triglyceride content, and hepatic triglyceride content (FIGS. 3I-K) while having no effect on glucose absorption (FIG. 7C).

Mfge8 Stimulates Fatty Acid Uptake Through a PI3 Kinase-mTORC2-AKT-Dependent Pathway.

Figure 4:
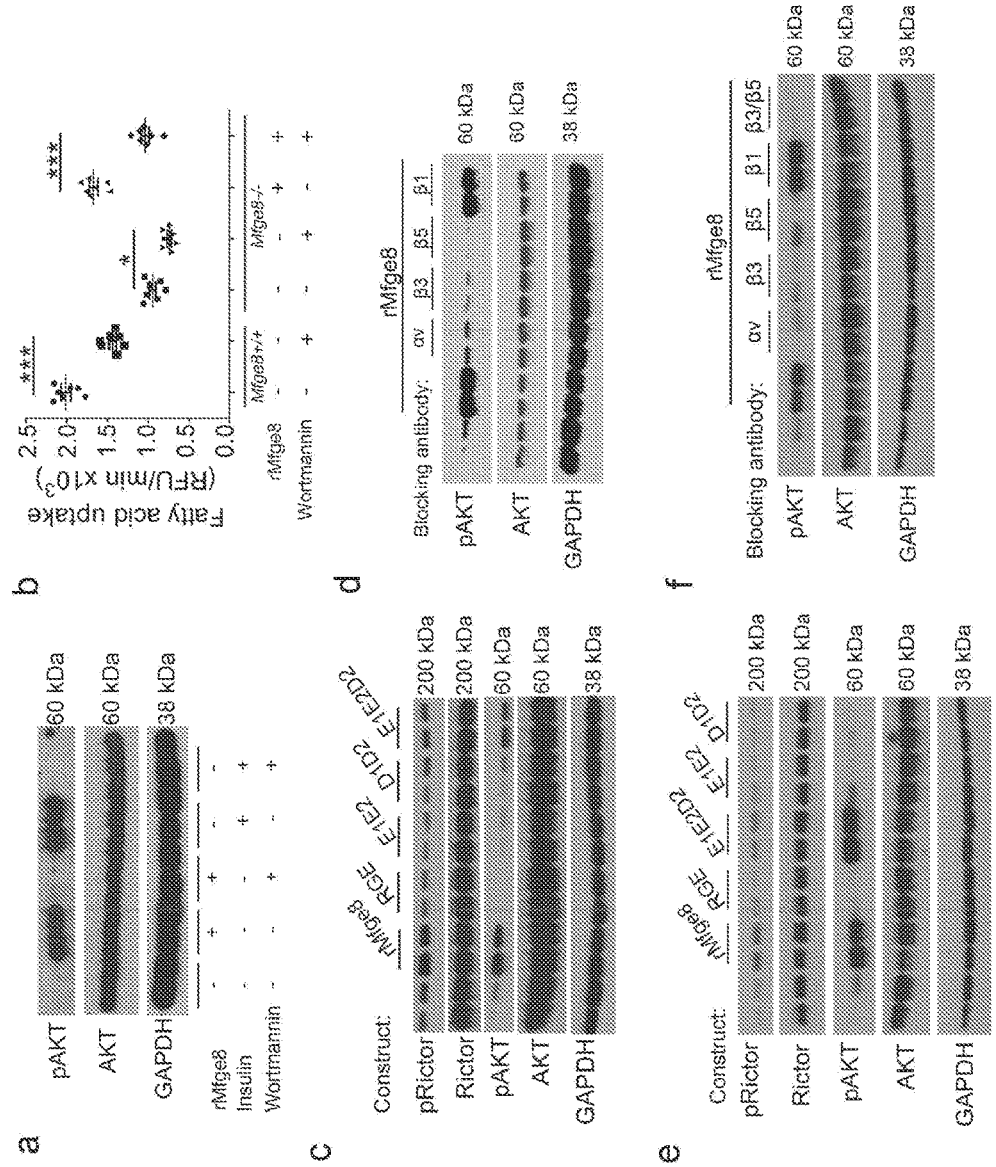
FIGS. 4A-4F. Mfge8 increases fatty acid uptake through an integrin-PI3K-AKT-dependent pathway. (A) Effect of rMfge8 (10 μg/mL) or insulin (10 μg/mL) with and without wortmannin (100 nM) on AKT phosphorylation. (B) Effect of wortmannin on fatty acid uptake in primary Mfge8+/+ and Mfge8−/− adipocytes and on Mfge8−/− adipocytes treated with rMfge8. N=7. *P<0.05, ***P<0.001. Data are expressed as mean±s.e.m. Each replicate represents an independent experiment. (C) Effect of mutated Mfge8 constructs on AKT and Rictor phosphorylation in 3T3-L1 adipocytes. (D) Effect of integrin blocking antibodies on AKT phosphorylation in 3T3-L1 adipocytes after treatment with rMfge8. (E) The effect of mutated Mfge8 constructs on phosphorylation of AKT and Rictor in HepG2 cells. (F) The effect of rMfge8 on AKT phosphorylation in the presence of integrin blocking antibodies in HepG2 cells.

PI3 kinase and AKT are integral parts of regulatory pathways in metabolism (Manning, B. D. & Cantley, L. C., *Cell* 129, 1261-1274 (2007); Li, X. et al., *Nature* 447, 1012-1016 (2007)). We therefore investigated whether the Mfge8-induced increase in fatty acid uptake was mediated through an AKT/PI3K axis. rMfge8 induced phosphorylation of AKT at serine 473 (s473) in 3T3-L1 cells and this effect was completely blocked by the PI3 kinase inhibitor wortmannin (FIG. 4A). Wortmannin also inhibited the ability of rMfge8 to increase fatty acid uptake in Mfge8−/− adipocytes treated with rMfge8 (FIG. 4B). AKT phosphorylation was dependent on an intact integrin binding motif and the presence of at least one discoidin domain (FIG. 4C) and was inhibited by blocking antibodies to the βv, β3, and β5 integrin subunits (FIG. 4D). mTOR Complex 2 (mTORC2) is the kinase complex primarily responsible for phosphorylation of AKT at s473 (Sarbassov, D. D. et al., *Science* 307, 1098-1101 (2005)). To determine whether Mfge8-induced AKT phosphorylation was mediated through mTORC2, we evaluated phosphorylation of rapamycin-insensitive companion of mTOR (Rictor) at threonine 1135. Rictor was phosphorylated by Mfge8 and phosphorylation required an intact integrin binding motif and at least one discoidin domain (FIG. 4C). Mfge8 also induced phosphorylation of AKT and Rictor in HepG2 cells by an integrin-dependent pathway (FIGS. 4E,F).

Mfge8 Stimulates Fatty Acid Uptake by Inducing Translocation of CD36 and FATP1 to the Cell Surface.

Figure 5:
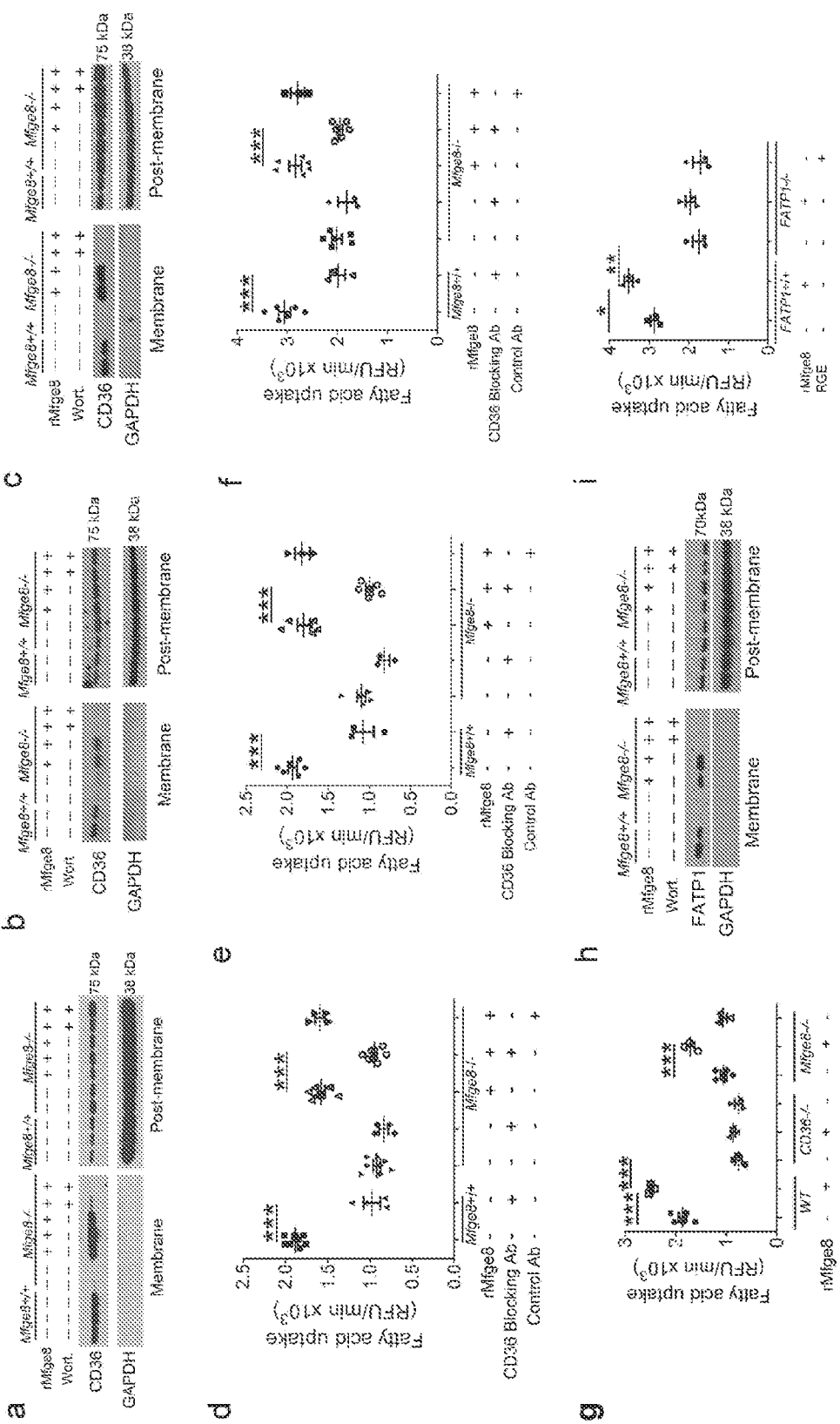
FIGS. 5A-5I. Mfge8 stimulates fatty acid uptake by inducing translocation of fatty acid transporters to the cell surface. (A-C) Plasma membrane and post membrane CD36 expression in primary Mfge8−/− and Mfge8+/+ adipocytes (A), hepatocytes (B), and enterocytes (C). Mfge8−/− cells were also incubated with rMfge8 or rMfge8 and wortmannin. (D-F) Effect of CD36 blocking antibody or control antibody on the ability of rMfge8 to increase fatty acid uptake in primary Mfge8−/− and Mfge8+/+ adipocytes (D), hepatocytes (E), and enterocytes (F), and on Mfge8+/+ adipocytes, hepatocytes, and enterocytes. N=3-4 for experiments with antibodies and 7-8 for experiments with and without rMfge8. (G) Effect of rMfge8 on fatty acid uptake in CD36+/+ and CD36−/− adipocytes. N=3 for experiments with CD36−/− cells and rMfge8 and 6 for experiments with Mfge8+/+ and Mfge8−/− cells, each replicate represents an independent experiment and data from different experiments were combined for statistical analysis. (H) Plasma membrane and post membrane expression of FATP1 in primary Mfge8−/− and Mfge8+/+ adipocytes, and Mfge8−/− adipocytes treated with rMfge8 or rMfge8 and wortmannin. (I) Effect of rMfge8 on fatty acid uptake in FATP1+/+ and FATP1−/− adipocytes. N=3, each replicate represents an independent experiment. *P<0.05, P<0.001, *P<0.0001. Data are expressed as mean±s.e.m.
Figure 6:
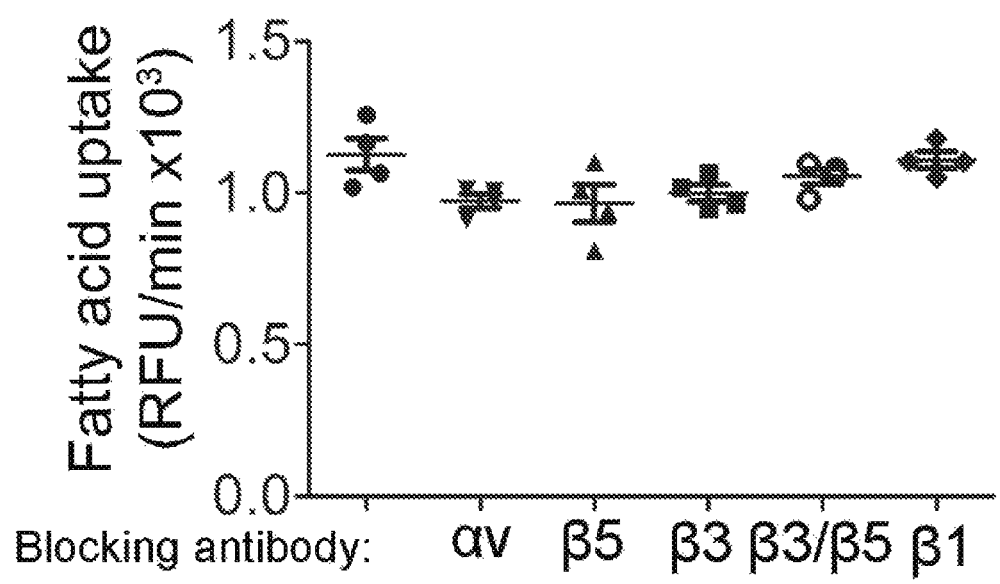
FIG. 6. Effect of integrin blocking antibodies on fatty acid uptake by Mfge8−/− adipocytes. Fatty acid uptake was measured in Mfge8−/− adipocytes in the presence of integrin blocking antibodies (20 μg/ml). N=4. Data are expressed as mean±s.e.m. Each replicate represents an independent experiment.

CD36 is a key mediator of fatty acid uptake (Ibrahimi, A. et al., *Proc Natl Acad Sci USA* 93, 2646-2651 (1996)) that is regulated by translocation from cytosolic stores to the cell surface (Glatz, J. F. et al., *Physiol Rev* 90, 367-417 (2010)). We therefore evaluated whether Mfge8 induced translocation of CD36 to the cell surface. In primary Mfge8−/− adipocytes, hepatocytes, and enterocytes there was a marked reduction in membrane CD36 (FIGS. 5A-C). The addition of rMfge8 increased membrane expression of CD36 in Mfge8−/− cells to WT levels, and this effect was completely inhibited by wortmannin. Incubation with a CD36 blocking antibody prevented rMfge8 from increasing fatty acid uptake in Mfge8−/− adipocytes, hepatocytes, and enterocytes (FIGS. 5D-F). Unlike WT adipocytes, rMfge8 did not significantly increase fatty acid uptake in CD36−/− adipocytes. FATP1 is a member of the FATP family and plays a key role in fatty acid transport in adipocytes. Like CD36, FATP1 is translocated from cytosolic pool to the cell surface for fatty acid transport (Stahl, A. et al., *Developmental cell* 2, 477-488 (2002)). Membrane expression of FATP1 was reduced in Mfge8−/− adipocytes, expression was increased by rMfge8, and this effect was inhibited by wortmannin (FIG. 5H). The addition of rMfge8 to FATP1−/− adipocytes did not significantly increase fatty acid uptake (FIG. 5I). Taken together, these data indicate that Mfge8 regulates fatty acid uptake by inducing translocation of the machinery of fatty acid uptake to the cell surface.

Mfge8−/− Mice are Protected from Weight Gain on a HFD Due to Impaired Fat Absorption.

To determine whether Mfge8-mediated fatty acid uptake contributes to the development of obesity in vivo, we evaluated weight gain in Mfge8−/− mice placed on a HFD. Male and female Mfge8−/− mice gained less weight as compared with controls over a 12 week period on a HFD. The eWAT of 20-week-old Mfge8−/− mice on a HFD weighed significantly less than control eWAT. There was a marked induction of Mfge8 protein in eWAT of WT mice on HFD. 20-week-old Mfge8−/− mice on a HFD or CD had smaller adipocytes and reduced hepatic triglyceride content (CD). The hearts of Mfge8−/− mice also had significantly reduced triglyceride content. To determine the body composition of Mfge8−/− mice on a HFD, we examined lean and fat mass using DEXA scanning 20-week old Mfge8−/− mice on HFD and 10- and 20-week old, but not 5-week-old, Mfge8−/− mice on a CD had significantly less total body fat and percent body fat. Since obesity is associated with insulin resistance, we performed insulin tolerance tests on Mfge8−/− mice. 20-week old Mfge8−/− mice on a HFD had increased insulin sensitivity compared to WT mice. 10-, but not 5-, week old Mfge8−/− mice on a CD had enhanced insulin sensitivity. To evaluate whether the decrease in body fat was secondary to impaired absorption of dietary fats, we measured stool triglyceride and energy content. Mfge8−/− mice on HFD had significantly higher stool triglyceride levels and caloric content as measured by bomb calorimetry.

Mfge8−/− Mice are Protected from Obesity-Induced Adipose Tissue Inflammation

Since obesity is associated with chronic inflammation (Weisberg, S. P. et al., *J Clin Invest* 112, 1796-1808 (2003)) and Mfge8 suppresses inflammation by multiple mechanisms (Kudo, M. et al., *Proc Natl Acad Sci USA* 110, 660-665 (2013)), we evaluated eWAT inflammation in Mfge8−/− mice on a HFD. There was a marked reduction in eWAT infiltrating macrophages by immunohistochemistry as well as a reduction in multiple immune populations as evaluated by flow cytometry in Mfge8−/− mice. Since Mfge8−/− mice develop age-dependent autoimmune disease (that is apparent at 40 weeks of age) (Hanayama, R. et al., *Science* 304, 1147-1150 (2004)), we evaluated whether 20-week old Mfge8−/− mice on a HFD had evidence of chronic immune activation that may have contributed to the decrease in body fat. We found no difference in the number or percent of activated splenic lymphocytes or total number of cells in the spleens of 20-week old Mfge8−/− mice on a HFD.

Mfge8 Deficiency does not Alter Energy Expenditure

We next examined whether differences in energy expenditure could account for the differences in body fat in Mfge8−/− mice. After 10 days on HFD, we placed 12-week-old Mfge8−/− and WT mice in clams metabolic cages for a period of 4 days. We found no difference in total oxygen consumption, oxygen consumption corrected for lean body mass, food intake, or ambulation when comparing Mfge8−/− and control mice. Finally, there was a modest increase in the respiratory exchange ratio in Mfge8−/− mice without changes in eWAT PGC1a expression. Collectively, these data indicate that the decrease in body fat in Mfge8−/− mice is not caused by exaggerated inflammation, an increase in energy expenditure, or an increase in fatty acid oxidation.

Discussion

The work presented here identifies a critical role for Mfge8 in regulating obesity through modulation of cellular uptake and storage of fatty acids. In the gastrointestinal tract, Mfge8 coordinates orderly absorption of dietary fats. Mfge8 deficiency leads to fat malabsorption, a reduction in total body fat, and protection from diet induced obesity (DIO). Importantly, Mfge8 also increases fatty acid uptake by adipocytes, cardiac myocytes and hepatocytes. While the in vivo sequelae of impaired fatty acid uptake by peripheral organs in Mfge8−/− mice is obscured by the malabsorption phenotype, the data suggests that under normal conditions (wild type mice and humans), Mfge8 is physiologically important for fat uptake in these tissues. This conclusion is supported by the following observations. Serum fatty acid levels are lower in Mfge8−/− mice after an olive oil bolus. However, when mice are fasted for 24 hours, serum fatty acid levels are significantly higher in Mfge8−/− mice consistent with impaired peripheral uptake of fatty acids released after catecholamine-induced lipolysis. There is a near 100-fold increase in adipose tissue Mfge8 expression when mice are placed on a HFD suggesting, as further discussed below, a key role for Mfge8 in persistent expansion of adipose tissue with progressive weight gain. Similarly, expression of Mfge8 and both the $\alpha v$ and $\beta 5$ integrin subunits are significantly increased in the adipose tissue of obese humans (Henegar, C. et al., *Genome Biol* 9, R14 (2008)). Mfge8 induces translocation of FATP1 to the cell surface, a fatty acid transport protein that is lacking in the intestine, but present in adipocytes and cardiac myocytes.

Fatty acid transporter translocation is a key regulatory step by which cellular uptake of fatty acids can be acutely modified in response to hormonal and metabolic cues (Bonen, A. et al., *J Biol Chem* 275, 14501-14508 (2000)). Insulin and muscle contraction increase fatty acid uptake in skeletal and cardiac muscle through this mechanism (Jain, S. S. et al., *FEBS Lett* 583, 2294-2300 (2009); Glatz, J. F. et al., *Physiol Rev* 90, 367-417 (2010)). The identification of additional regulatory pathways that modulate this process has been elusive. While both insulin and Mfge8 induce translocation of fatty acid transporters through PI3 kinase-dependent phosphorylation of AKT (Stahl, A. et al., *Developmental cell* 2, 477-488 (2002); Chabowski, A. et al., *Am J Physiol Endocrinol Metab* 287, E781-789 (2004)), there are some key differences between their roles in fatty acid uptake. In the gastrointestinal tract, Mfge8 mediates absorption of dietary triglycerides while insulin regulates nutrient deposition in tissues after absorption from the intestine. Another distinction is apparent in obese adipose tissue. While insulin promotes lipogenesis by inducing de novo triglyceride synthesis (Wakil, S. J. et al., *Annu Rev Biochem* 52, 537-579 (1983)), increasing fatty acid uptake (Stahl, A. et al., *Developmental cell* 2, 477-488 (2002)), and inhibiting lipolysis (Jensen, M. D. et al., *Diabetes* 38, 1595-1601 (1989)), obesity is associated with adipocyte insulin resistance (Smith, U., *Int J Obes Relat Metab Disord* 26, 897-904 (2002)). Adipocytes from diabetic patients have impaired downstream signaling after insulin receptor binding, resulting in reduced PI3 kinase activity (Rondinone, C. M. et al., *Proc Natl Acad Sci USA* 94, 4171-4175 (1997)). This raises an interesting paradox: how does insulin continue to promote adipocyte enlargement and obesity by stimulating cells that are known to be insulin-resistant? Our data raise the interesting possibility that the marked increase in adipocyte Mfge8 expression during obesity may supply the signal that promotes fatty acid uptake in insulin-resistant adipocytes, thereby perpetuating the adipose hypertrophy characteristic of obesity. Finally, unlike insulin, Mfge8 systemically induces fatty acid uptake without directly affecting glucose uptake, thereby providing a mechanism to dissociate regulation of these two major components of nutrient metabolism.

The relative contribution of Mfge8-mediated CD36 translocation to increased fatty acid uptake induced by Mfge8 in different organ system is an area of active investigation. In adipocytes, our data indicate that Mfge8 regulates both FATP1 and CD36 translocation. The roles of CD36 and FATP1 in promoting fatty acid uptake are well established in adipocytes (Coburn, C. T. et al., *J Biol Chem* 275, 32523-32529 (2000); Wu, Q. et al., *Mol Cell Riot* 26, 3455-3467 (2006)), and cardiac myocytes (Coburn, C. T. et al., *J Biol Chem* 275, 32523-32529 (2000); Tanaka, T. et al., *J Lipid Res* 42, 751-759 (2001)) and are consistent with a model whereby the effect of Mfge8 on fatty acid uptake in these tissues is mediated through translocation of FATP1 and CD36 to the cell surface. Whether the effect of Mfge8 on fatty acid uptake in the intestinal tract is primarily mediated through CD36 is less clear. Absorption of dietary fats is a multistep process that begins with luminal breakdown of ingested triglycerides into free fatty acids that are subsequently taken up by enterocytes where they are re-esterified and secreted as chylomicrons (Bamba, V. & Rader, D. J., *Gastroenterology* 132, 2181-2190 (2007)). CD36 modulates both absorption of dietary fats and secretion of triglycerides by intestinal epithelial cells (Drover, V. A. et al., *J Biol Chem* 283, 13108-13115 (2008); Drover, V. A. et al., *J Clin Invest* 115, 1290-1297 (2005); Nassir, F. et al., *J Biol Chem* 282, 19493-19501 (2007)). The impairment in Mfge8−/− enterocyte fatty acid uptake in vitro and the increase in fecal energy content in Mfge8−/− mice suggest that the main effect of Mfge8 is to stimulate uptake of fatty acids rather than regulate secretion of chylomicrons. As we found in adipocytes, Mfge8 may interact with additional fatty acid transporters in the gastrointestinal tract leading to overlapping but not identical phenotypes in enteral fat absorption in Mfge8−/− and CD36−/− mice. While the protection from the DIO in Mfge8−/− mice is reminiscent of MGAT2−/− mice, MGAT2−/− mice have a delay in absorption rather than malabsorption of dietary fats. Yen, C. L. et al., *Nat Med* 15, 442-446 (2009)).

Our work also identifies an important role for integrins in regulating lipid homeostasis. We show that both the αvβ3 and αvβ5 integrins induce AKT phosphorylation via PI3 kinase and mTORC2. Of note, integrins are overexpressed in many malignancies (Mizejewski, G. J., *Proc Soc Exp Biol Med* 222, 124-138 (1999)) and overexpression is important in the interaction of malignant cells with the extracellular matrix relative to both cancer growth and metastasis (Zhao, Y. et al., *Cancer Res* 67, 5821-5830 (2007)). Our data raise the possibility that integrin overexpression in malignancies may increase tumor cell fatty acid uptake. This may be particular importance in malignancies such as prostate cancer where cells preferentially metabolize fatty acids. (Liu, Y., *Anticancer Res* 30, 369-374 (2010)) and overexpress the αvβ3 integrin (Zheng, D. Q., *Cancer Res* 59, 1655-1664 (1999)).

Our results provide a mechanism to explain the recent observations that Mfge8 is located in a region linked with susceptibility to obesity in humans (Rankinen, T. et al., *Obesity* (Silver Spring) 14, 529-644 (2006)) and that adipose expression of Mfge8 is increased in human obesity (Henegar, C. et al., *Genome Biol* 9, R14 (2008)). Collectively, our data indicate that Mfge8 ligation of integrin receptors regulates body fat content by regulating the uptake of fatty acids in the alimentary tract and in peripheral tissues. From the therapeutic viewpoint, this pathway can be targeted for the treatment of malabsorption syndromes or obesity. To our knowledge, we show the first evidence of a pathway that can augment absorption of dietary fats and serve as a target for the treatment of fat malabsorption. In addition, inhibition of the Mfge8-dependent pathway will provide a novel therapeutic target for the treatment of obesity that directly inhibits the molecular pathways of fat absorption in the gastrointestinal tract. A better understanding of the mechanisms that regulate fat uptake and storage is of significant interest in the light of the high morbidity, mortality and economic burden associated with obesity and obesity-related disease.

Supplemental Methods

Mice.

All animal experiments were approved by the UCSF Institutional Animal Care and Use Committee in adherence to NIH guidelines and policies. In vivo studies were conducted with two different lines of mice deficient in Mfge8. Some studies were carried out on Mfge8−/− mice created by a gene disruption vector. These mice have been extensively characterized and have the same phenotypes as Mfge8−/− mice created by homologous recombination (Silvestre, J. S. et al., *Nat Med* 11, 499-506 (2005); Atabai, K. et al., *Mol Biol Cell* 16, 5528-5537 (2005)). Mice were backcrossed 10 generations into the C57bl/6 background and bred as Mfge8−/− breeding pairs and Mfge8+/+ breeding pairs. In a subset of studies, Mfge8−/− and Mfge8+/− breeding pairs were used to generate sibling littermates from the same cage. A second line of Mfge8 mice created by homologous recombination was obtained from RIKEN (Hanayama, R. et al., *Nature* 417, 182-187 (2002)). These mice were bred as Mfge8−/− and Mfge8+/− breeding pairs and used in some studies and as Mfge8−/− and Mfge8+/+ breeding pairs for studies used in FIGS. 3A-3K and, and for harvesting of all primary cells used in in vitro studies. All mice were age- (6-8 weeks of age unless otherwise noted) and sex-matched. β3−/− and β5−/− mice in the 129 SVEV strain have been previously described (Huang, X. et al., *Mol Cell Biol* 20, 755-759 (2000); Su, G. et al., *Am J Respir Crit Care Med* 185, 58-66 (2012)). CD36−/− mice were generously provided by Roy Silverstein and were in the C57bl/6 background. FAP1−/− mice were also in the C57bl/6 background (Wu, Q. et al., *Mol Cell Biol* 26, 3455-3467 (2006)). For FIGS. 3C-3I investigator were blinded to genotypes until statistical analysis of the data. Investigators were not blinded as to genotype in animal studies that involved weighing mice on a high-fat diet, obtaining insulin tolerance tests, and determining body composition by Dexa scan. Investigators were blinded to the mouse genotypes for the energy expenditure experiments which were done by a core facility.

High-Fat Diet.

8 to 10 week-old mice were placed on a high-fat formula containing 60% fat calories (Research Diets, Inc.) for 12 weeks. The control diet contained 9% fat calories (PMI). Mice were housed in groups of 5 mice per cage for diet experiments including weights, insulin tolerance tests, Dexa scanning for body composition, adipocyte size quantification, and hepatic triglyceride content with each cage of 5 mice representing an independent experiment.

Fluorescent Fatty Acid Uptake Assay.

Uptake of fatty acids by differentiated 3T3-L1 adipocytes or primary mouse adipocytes was assessed using a QBT Fatty Acid Uptake Kit (Molecular Devices). Cells were plated in triplicate in 96-well plates at a concentration of 25,000 cells per well in 100 μl of DMEM/10% FCS. Plates were centrifuged at 1000 rpm for 4 minutes and incubated at 37° Celsius for 4-5 hours. Cells were then serum deprived for 1 hour before treatment with recombinant proteins for 30 minutes followed by the addition of QBT Fatty Acid Uptake solution. In experiments using function-blocking antibodies, antibodies against mouse integrins αv (clone RMV-7) (Takahashi, K. et al., *J Immunol* 145, 4371-4379 (1990)) β3 (clone 2C9.G2; BD Biosciences) (Ashkar, S. et al., *Science* 287, 860-864 (2000)), β5 (clone ALULA) (Su, G. et al., *American journal of respiratory cell and molecular biology* 36, 377-386 (2007)), 131 (clone HA2/5; BD Biosciences, anti-rat with cross-reactivity with mouse (Zovein, A. C. et al., *Developmental cell* 18, 39-51 (2010)), CD36 (clone MF3; Abcam) (Helming, L. et al., *Journal of cell science* 122, 453-459 (2009)), human integrins αv (clone L230) (Thomas, G. J. et al., *British journal of cancer* 87, 859-867 (2002)), β3 (clone Axum-2) (Su, G. et al., *Am J Respir Crit Care Med* 185, 58-66 (2012)), β5 (clone ALULA), β1 (clone P5D2), cycloRGD and cycloRAD (BACHEM) were added to cells after serum deprivation and cells were incubated for 20 minutes at 4° Celsius prior to addition of recombinant proteins. Plates were incubated in a fluorescent plate reader at 37° Celsius and kinetic readings were acquired every 20 seconds for 30 minutes. Fluorescence values were plotted against time and data was expressed as relative fluorescent units per minutes×$10^3$.

3T3-L1 Cell/HepG2 Cell Culture.

3T3-L1 (Zen-Bio) fibroblasts were differentiated into adipocytes as described previously (Liao, J. et al., *J Lipid Res* 46, 597-602 (2005)). Briefly, 3T3-L1 fibroblasts were cultured to confluence on 10 cm tissue culture plates or in 6-well tissue culture dishes in DMEM supplemented with 10% FBS and 25 mM HEPES (normal medium). 2 days after reaching confluence, media was change and 3-isobutyl-1methylxanthine (Calbiochem), dexamethasone (Sigma), and insulin (Sigma) were added to the normal medium at concentrations of 0.5 mM, 1 μM, and 5 μg/mL, respectively, to induce adipocyte differentiation. After 2 days (and every 2 days thereafter), media was replaced with normal medium supplemented with 5 µg/mL insulin. Cells were harvested for use 6-10 days after differentiation. The human hepatocellular carcinoma cell line HepG2 was a generous gift of Dr. Ethan Weiss. Cells were propagated in Eagle's MEM supplemented with 10% fetal bovine serum.

Olive Oil Gavage and Serum Triglyceride and Fatty Acid Content.

6-8 week-old mice were fasted for 4 hours and then gavaged with 15 µL olive oil per gram body weight. Mice had access to water but not food for the remainder of the experiment. In the experiments in FIGS. 3C and 3F, 50 µg/kg body weight of recombinant protein was mixed into olive oil and administered immediately to mice by gavage. In blocking antibody experiments, integrins αv (clone RMV-7) and β5 (clone ALULA) were administered by gavaging mice with 100 µL water containing 0.5 µg antibody per gram body weight 30 minutes before olive oil gavage. Triglyceride content of serum was assayed using a commercially available kit (Sigma-Aldrich) and fatty acid concentrations were quantified by Wako (Rabot, S. et al., *FASEB J* 24, 4948-4959 (2010)).

Quantification of Liver, Intestinal, and Fecal Triglyceride Content.

After experiments described above, samples from the left lobe of the liver and the proximal small intestine were isolated and rapidly frozen in liquid nitrogen for triglyceride content assays. Control mice were starved for 8 hours before their organs were harvested as above. Triglyceride content of the intestine (Uchida, A. et al., *Front Physiol* 3, 26) and liver (Kim, K. Y. et al., *J Clin Invest* 121, 3701-3712 (2011)) and fecal samples Kim, K. Y. et al., *J Clin Invest* 121, 3701-3712 (2011)) were quantified as described previously.

Glucose Gavage and Blood Glucose Measurement.

6-8 week-old mice were fasted for 4 hours and then gavaged with 1.5 mg glucose per gram body weight. In the experiments in FIG. 7A, 50 µg/kg body weight of recombinant protein was mixed into glucose solution and administered immediately to mice by gavage. In blocking antibody experiments, integrins αv (clone RMV-7) and β5 (clone ALULA) were administered orally with 100 µL water containing 0.5 µg antibody per gram body weight 30 minutes before glucose gavage. Blood glucose levels were measured by sampling from the tail vein of mice from 0-60 minutes after glucose administered.

Fecal Fatty Acid Content.

6-8 week-old mice were fasted for 4 hours and then gavaged with 2 µg BODIPY per gram body weight. Feces were collected from 20 minutes to 4 hours after BODIPY administered. 50 mg of feces was homogenized in PBS contained 30 mM HEPES, 57.51 mM $MgCl_2$ and 0.57 mg/ml BSA with 0.5% SDS and sonicated for 30 seconds, and then centrifuged at 1000 g for 10 minutes. Supernatants were transferred to 96 well plates and Fluorescence values were measured immediately using a fluorescence microplate reader for endpoint reading (Molecular Devices).

Primary Adipocyte, Hepatocyte, Enterocyte, and Adipocyte Progenitor Culture.

Adipocytes.

Primary mouse adipocytes were obtained from epididymal fat pads by collagenase digestion in Krebs-HEPES (KRBH) buffer followed by filtering through a 100 µm strainer which was then washed with an additional 7.5 mL KRBH buffer. Adipocytes were allowed to float to the top of the mixture for 5 minutes, and the solution under the adipocyte layer was removed with a syringe. The adipocytes were washed with 10 mL KRBH and again allowed to float to the surface, at which point the solution was again removed. This process was repeated for a total of 3 washes. After the last aspiration, adipocytes were resuspended in 0.5-1.0 mL and counted.

Adipocyte Progenitors.

Primary mouse adipocyte progenitors from the vascular stromal fraction were isolated and cultured as reported previously (Tseng et al., 2008). In brief, subcutaneous white adipose tissue was removed, minced and digested with 1 mg/ml collagenase for 45 min at 37° C. in DMEM/F12 medium containing 1% BSA and antibiotics. Digested tissues were filtered through sterile 150 µm nylon mesh and centrifuged at 250 g for 5 min. The floating fractions consisting of adipocytes were discarded and the pellets representing the stromal vascular fractions were resuspended in erythrocyte lysis buffer (154 mM $NH_4Cl$, 10 mM $KHCO_3$, 0.1 mM EDTA) for 10 min to remove red blood cells. The cells were further centrifuged at 500 g for 5 min, plated at $8\times10^5$ per well of a 24-well plate, and grown at 37° C. in DMEM/F12 supplemented with 10% FBS at 37° C. 2 days after cells reached 100% confluence, cells were treated with 1 µM rosiglitazone and 5 µg/mL insulin to induce terminal differentiation.

Primary Hepatocytes.

The liver was pre-perfused through the portal vein with calcium-free buffer (0.5 mM EDTA, HBSS without $Ca^{2+}$ and $Mg^{2+}$) and next perfused with collagenase (3.5 U/ml Collegenase II (Worthington) 25 mM HEPES, HBSS with $Ca^{2+}$ and $Mg^{2+}$). Parenchymal cells were purified by Percoll buffer (90% Percoll (Sigma), 1×PBS) at low-speed centrifugation (1500 rpm for 10 min). Viability of isolated hepatocytes was determined by Trypan blue staining (around 85%) and cell density was approximately 60% confluence. Cells were plated in collagen-I-coated dishes and cultured at 37° C. in a humidified atmosphere of 95% $O_2$ and 5% $CO_2$ in growth medium (Huang, P. et al., *Nature* 475, 386-389 (2011)).

Primary Enterocytes.

The proximal small intestine was collected from anesthetized mice, and the luminal contents were emptied, washed with 115 mM NaCl, 5.4 mM KCl, 0.96 mM $NaH_2PO_4$, 26.19 mM $NaHCO_3$, and 5.5 mM glucose buffer, pH 7.4, and gassed for 30 minutes with 95% $O_2$ and 5% $CO_2$. The proximal small intestines were then filled with buffer containing 67.5 mM NaCl, 1.5 mM KCl, 0.96 mM $NaH_2PO_4$, 26.19 mM $NaHCO_3$, 27 mM sodium citrate, and 5.5 mM glucose, pH 7.4, saturated with 95% $O_2$ and 5% $CO_2$, and incubated in a bath containing oxygenated saline at 37° C. with constant shaking After 15 minutes, the luminal solutions were discarded and the intestines were filled with buffer containing 115 mM NaCl, 5.4 mM KCl, 0.96 mM $NaH_2PO_4$, 26.19 mM $NaHCO_3$, 1.5 mM EDTA, 0.5 mM dithiothreitol, and 5.5 mM glucose, pH 7.4, saturated with 95% $O_2$ and 5% $CO_2$, and bathed in saline as described above. After 15 minutes, the luminal contents were collected and centrifuged (1,500 rpm, 5 minutes, room temperature), and the pellets were resuspended in DMEM saturated with 95% $O_2$ and 5% $CO_2$=(Anwar, K. et al., *J Lipid Res* 48, 2028-2038 (2007)).

Primary Cardiomyocytes.

Hearts were immersed in ice-cold calcium-free perfusion buffer containing (in mmol/L) NaCl 120.4, KCl 14.7, $KH_2PO_4$ 0.6, $Na_2HPO_4$ 0.6, 5 $MgSO_4$-$7H_2O$ 1.2, Na-HEPES 10, $NaHCO_3$ 4.6, taurine 30, butanedione monoxime (BDM) 10, glucose 5.5, and then perfused through the aorta with calcium-free perfusion buffer (3 ml/minutes) for 4 minutes, then switched to calcium-free digestion buffer (perfusion buffer containing collagenase II [2 mg/ml] from Worthington Biochemical) for 10 minutes. This was followed by perfusion with digestion buffer containing 100 µmol/L $CaCl_2$ for another 8-10 minutes. Hearts were removed from the perfusion apparatus and placed in a 10 cm Petri dish containing 2 ml digestion buffer and 3 ml of stop buffer (perfusion buffer supplemented with 10% FBS). The atria were removed and the ventricles were pulled into 10-12 equally sized pieces. Tissue was then gently dispersed into cell suspension using plastic transfer pipettes. The cell suspension was collected in a 15 ml falcon tube, brought to 10 ml with stop buffer and centrifuged at 40×g for 3 minutes. Damaged myocytes and non-myocytes were removed by a series of washes in 10 ml stop buffer containing, sequentially, 100, 400, or 900 µmol/L $CaCl_2$. Cardiomyocytes were pelleted by centrifugation at 40×g for 3 minutes after each wash and plated in laminin coated dishes (Smyth, J. W. et al., Circ Res 110, 978-989 (2012)).

Recombinant Protein Production.

Recombinant protein constructs were created and expressed in High 5 cells as previously described (Atabai, K. et al., J Clin Invest 119, 3713-3722 (2009)). For studies using different recombinant constructs the molar equivalent of 10 µg/mL of full-length recombinant Mfge8 was used for each construct.

Western Blot.

Following tissue preparation and SDS-PAGE, membranes were incubated with a polyclonal antibody against Akt (Cell Signaling Technology), or Rictor (Cell Signaling); Anti-PGC1 alpha antibody (abcam); a monoclonal antibody against Phospho-Akt Ser473 (Cell Signaling), Phospho-Rictor Thr1135 (Cell Signaling), GAPDH (Cell Signaling), or Mfge8 (R&D Systems). For evaluation of total AKT and total Rictor, membranes that been blotted for phospho-AKT and phospho-Rictor were stripped and reprobed. Plasma membrane and post-plasma membrane fractions were isolated as previously described (Nishiumi, S. & Ashida, H., Biosci Biotechnol Biochem 71, 2343-2346 (2007)).

Immunohistochemistry.

5 µm sections were boiled for 15 minutes in 10 mM sodium citrate (pH 6) for antigen retrieval and blocked with $H_2O_2$ in methanol and subsequently 2% BSA. Rabbit anti-MAC2 antibody (Cedarlane, CL8942AP) directed against MAC2 was used at 1:3800 dilution in TBS and 0.5% tween, followed by a 1:200 biotinylated anti-rabbit secondary antibody (Vector), ABC reagent (Vector) and liquid diaminobenzidine substrate (Sigma).

Morphometric Analysis.

Paraffin embedded eWAT sections from 5 CD and 10 HFD mice were stained with H&E. For each section 5 high-power field (HPF) pictures were taken at 100× magnification. The average number of adipocytes per HPF for each section was counted and the diameter of each adipocyte was measured using Image-Pro Plus MDA. Investigators were blinded to genotype during quantification.

Flow Cytometry.

Epididymal fat pads were dissected, weighed, and placed in a buffered collagenase solution for homogenization using a GentleMACS tissue dissociator. Homogenized tissue was incubated at 37° C. on a rotating shaker at 250 rpm for 30 minutes, then passed through a 40 um strainer and rinsed with 10 mL ice-cold PBS. After a red blood cell lysis step, cells were stained for viability using a LIVE/DEAD aqua fixable stain kit (Invitrogen, Carlsbad, Calif.) and then for the following stains to identify macrophage subtype and eosinophil populations: CD45 (clone 30-F11, BioLegend, San Diego, Calif.), CD11b (clone M1/70, BioLegend), F4/80 (clone BM8, BioLegend), CD11c (clone N418, BioLegend), CD301 (clone ER-MP23, AbdSerotec, Oxford, United Kingdom), Siglec (clone E50-2440, BD Pharmingen, San Diego, Calif.). A second set of cells from the fat pads were similarly stained for viability and then with the following antibodies to identify lymphocyte populations: CD45, CD4 (clone RM4-4, BioLegend), CD44 (clone IM7, Ebioscience), CD62L (clone MEL-14, BD Pharmingen), and FoxP3 (clone FJK-16s, Ebioscience, San Diego, Calif.). Spleens were removed after sacrificing ironic within. The splenocytes were treated to lyse red blood cells and subsequently stained for viability and the lymphocyte markers detailed above. Flow cytometry was performed on a BD FACS flow cytometer and analyzed using FlowJo Software (Tree Star Inc., Ashland, Oreg.).

Body Fat Analysis.

Bone, lean, and fat mass analysis was performed with GE Lunar PIXImus II Dual Energy X-ray Absorptiometer.

CLAMS Metabolic Cage Analysis.

Mice were placed in single housing cages for 5 days prior to initiating experimental analysis for a period of 96 hours. Mice were on a HFD for 10 days prior to initiating the analysis. The following variables were measured: food and water intake, oxygen consumption ($VO_2$) and carbon dioxide production ($VCO_2$) (at 13 minute intervals), and locomotor activity. Infrared beams monitored movement in the X, Y, and Z directions. The data presented was from the last 48 hours of the analysis (Sutton, G. M. et al., Endocrinology 147, 2183-2196 (2006)).

Measurements of Fecal Energy Content.

Feces from mice on a HFD were freeze dried (samples from 2 mice were combined for each sample) and pulverized with a ceramic mortar and pestle. Caloric content of feces was measured with an 1108 Oxygen Combustion Bomb calorimeter.

Insulin Tolerance Tests.

For insulin tolerance test, mice were fasted for 5 hours after which they were injected with 1.5 U/kg of insulin IP. Blood was collected from the tail vein immediately before injection and then again after 15, 30, 60, and 90 minutes for evaluation of blood glucose.

Statistical Analysis

Data were assessed for normal distribution and similar variance between groups using Graphpad Prism 6.0. One-way ANOVA was used to make comparisons between multiple groups. When the ANOVA comparison was statistically significant (P<0.05), further pairwise analysis was performed using a Bonferroni t-test. 2-sided Student's t-test, Mann-Whitney t-test or unpaired t-test with Welch's correction was used for comparisons between 2 groups depending on the distribution and variance of the data. GraphPad Prism 6.0 was used for all statistical analysis. All data are presented as mean±s.e.m. Sample size for animal experiments were selected based on numbers typically used in the literature. There was no randomization of animals.

Example 2: Mfge8 Modulates Glucose Uptake In Vitro and In Vivo

This example illustrates that the administration of recombinant Mfge8 (rMfge8) induces acute insulin resistance in cultured adipocytes and in vivo, while the administration of αv or β5 integrin blocking antibodies significantly increased the effect of insulin on glucose uptake in vitro and in vivo. This example also shows that IP co-administration of rMfge8 and insulin in mice resulted in significantly higher serum glucose levels as compared with insulin injection alone. Furthermore, pretreatment with αv or β5 integrin blocking antibody prior to insulin injection resulted in significantly lower serum glucose levels after insulin injection as compared to insulin injection alone.

Figure 9:
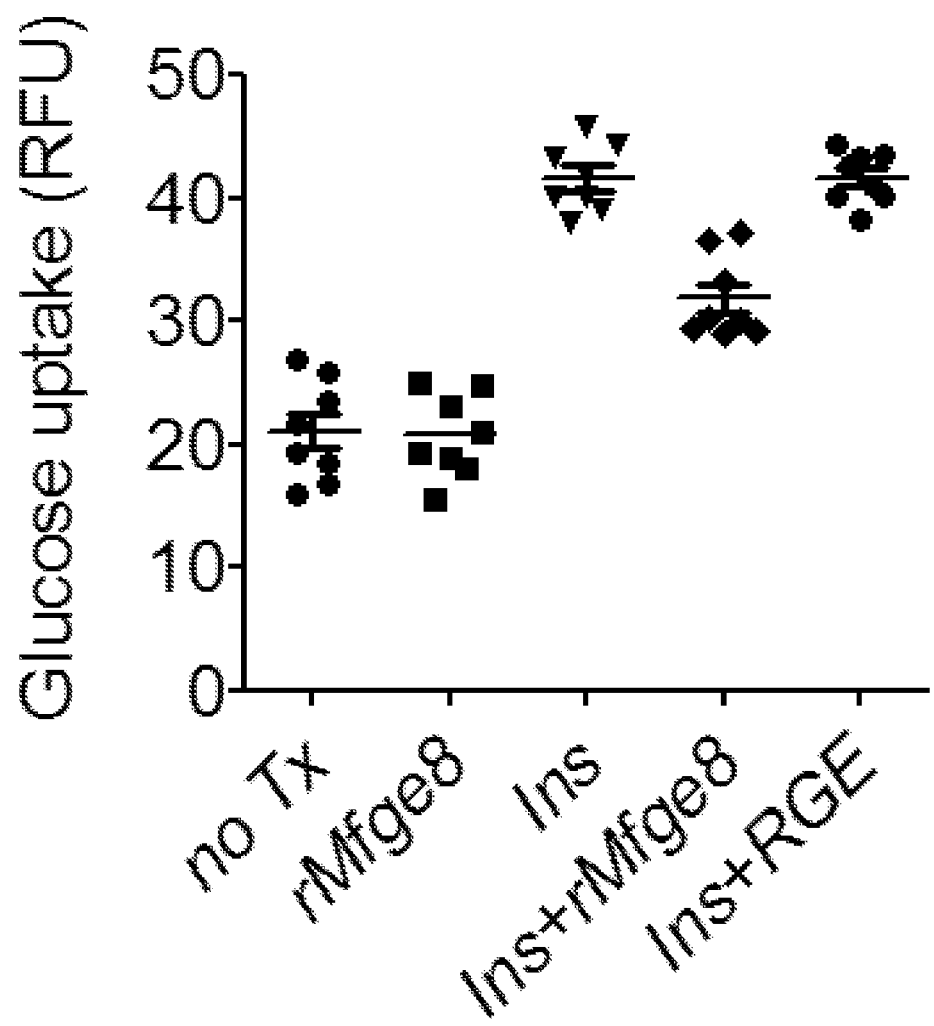
FIG. 9 shows that Mfge8 induces insulin resistance in 3T3-L1 adipocytes. Glucose uptake in 3T3-L1 adipocyte with and without 20 min treatment with recombinant Mfge8 or RGE (10 μg/ml) and insulin (1 μM) or both Mfge8 and insulin (n=8, P<0.05). Data are expressed as mean±s.e.m. Each replicate represents an independent experiment.

FIG. 9 shows that Mfge8 induces insulin resistance in 3T3-L1 adipocytes. Glucose uptake in 3T3-L1 adipocyte with and without 20 min treatment with recombinant Mfge8 or RGE (10 µg/ml) and insulin (1 µM) or both mfge8 and insulin (n=8, P<0.05). Data are expressed as mean±s.e.m. Each replicate represents an independent experiment.

Figure 10:
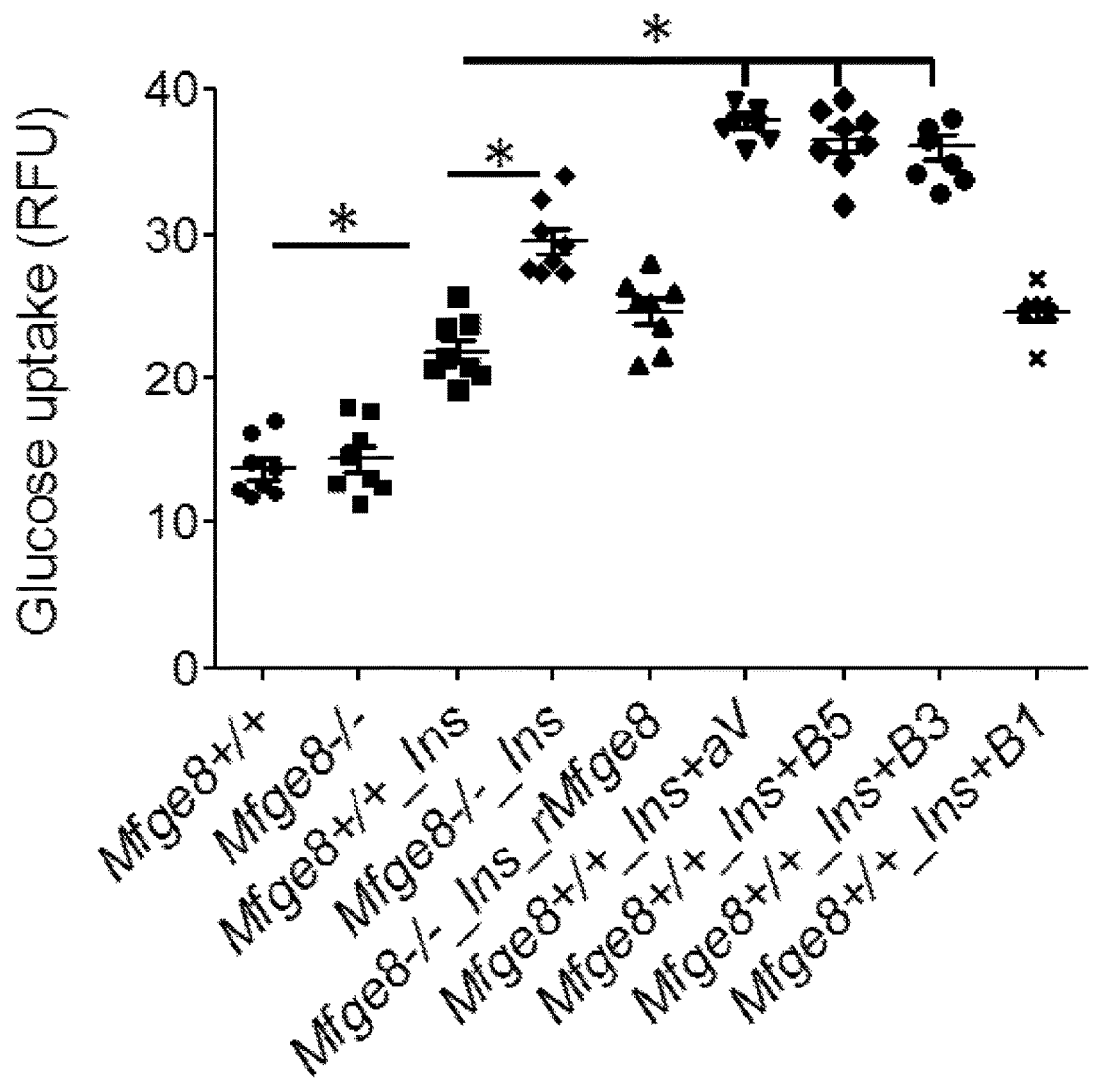
FIG. 10 illustrates that integrin receptor blockade enhances insulin sensitivity in primary adipocytes. Glucose uptake in Mfge8−/− and Mfge8+/+ primary adipocytes, with and without 20 min treatment with insulin (1 μM) and effect of pretreatment with integrin blocking antibodies (0.5 μg/g, IP, 15 min before insulin) on glucose uptake in Mfge8+/+ adipocytes. Data are expressed as mean±s.e.m. Each replicate represents an independent experiment (n=8, P<0.05). Pretreatment with αv, b3 or b5 integrin blocking antibody prior to insulin injection resulted in significantly lower serum glucose levels after insulin injection as compared with insulin injection alone.

FIG. 10 shows that integrin receptor blockade enhances insulin sensitivity in primary adipocytes. Glucose uptake in Mfge8−/− and Mfge8+/+ primary adipocytes, with and without 20 min treatment with insulin (1 µM) and effect of pretreatment with integrin blocking antibodies (0.5 µg/g, IP, 15 min before insulin) on glucose uptake in Mfge8+/+ adipocytes. Data are expressed as mean±s.e.m. Each replicate represents an independent experiment (n=8, P<0.05). Pretreatment with αv, b3 or b5 integrin blocking antibody prior to insulin injection resulted in significantly lower serum glucose levels after insulin injection as compared with insulin injection alone.

Figure 11:
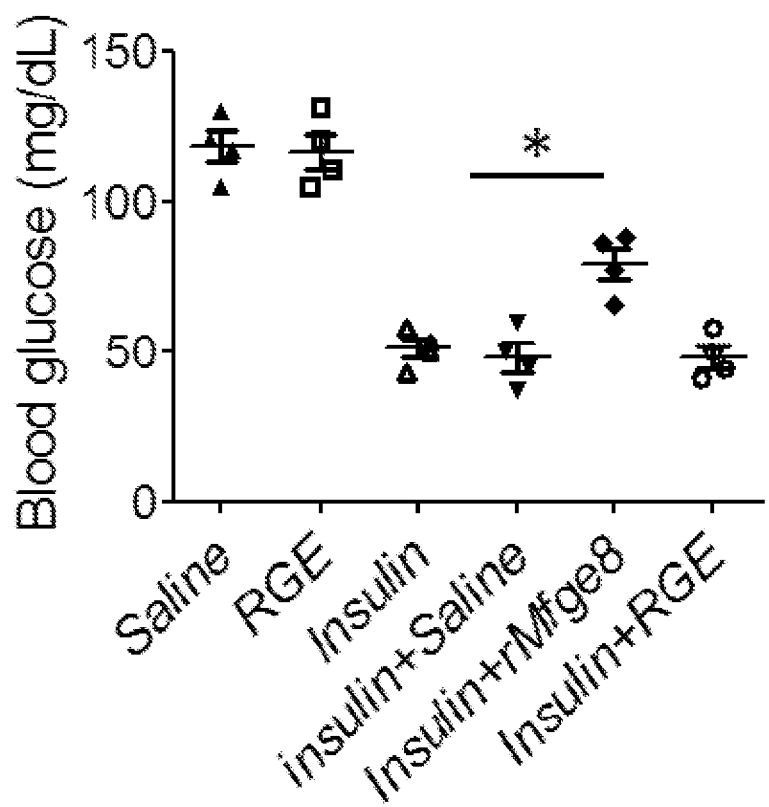
FIG. 11 shows that Mfge8 induces acute insulin resistance in vivo. 8-week-old Mfge8−/− and Mfge8+/+ control mice were fasted for 4 hours, then blood glucose was measured 15 min after IP injection of insulin (1 U/kg), saline, RGE (50 μg/kg) or a combination of insulin (1.5 U/Kg) and rMfge8 or RGE construct (50 μg/kg). Data are expressed as mean±s.e.m. Each replicate represents an independent experiment (n=4, P<0.05).

FIG. 11 shows that Mfge8 induces acute insulin resistance in vivo. 8-week-old Mfge8−/− and Mfge8+/+ control mice were fasted for 4 hours, then blood glucose was measured 15 min after IP injection of insulin (1 U/kg), saline, RGE (50 µg/kg) or a combination of insulin (1.5 U/Kg) and rMfge8 or RGE construct (50 µg/kg). Data are expressed as mean±s.e.m. Each replicate represents an independent experiment (n=4, P<0.05).

Figure 12:
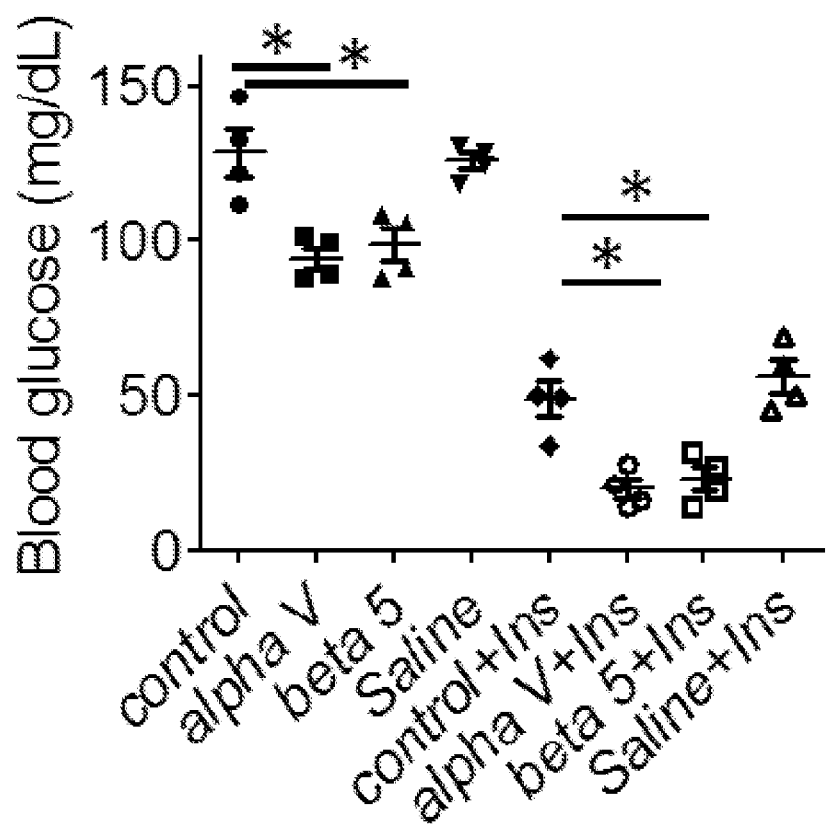
FIG. 12 shows that integrin blockade induces acute insulin sensitivity in vivo. 8-week-old Mfge8−/− and Mfge8+/+ control mice were fasted for 4 hours, then received blocking antibodies (0.5 µg per gram body weight)(αv (clone RMV-7) and βv (clone ALULA)) IP. 15 min prior insulin (1 U/kg) or saline, blood glucose was measured 15 min after IP injection of insulin (1 U/kg) or saline. Data are expressed as mean±s.e.m. Each replicate represents an independent experiment (n=4, P<0.05).

FIG. 12 shows that integrin blockade induces acute insulin sensitivity in vivo. 8-week-old Mfge8−/− and Mfge8+/+ control mice were fasted for 4 hours, then received blocking antibodies (0.5 µg per gram body weight) (αv (clone RMV-7) and βv (clone ALULA)) IP. 15 min prior insulin (1 U/kg) or saline, blood glucose was measured 15 min after IP injection of insulin (1 U/kg) or saline. Data are expressed as mean±s.e.m. Each replicate represents an independent experiment (n=4, P<0.05).

While recombinant Mfge8 (rMfge8) had no effect on baseline glucose uptake, rMfge8 significantly inhibited while αv or 05 integrin blocking antibodies significantly increased the effect of insulin on glucose uptake in both 3T3-L1 adipocytes and primary WT adipocytes. IP co-administration of rMfge8 and insulin in mice resulted in significantly higher while pretreatment with αv or 05 integrin blocking antibody prior to insulin injection resulted in significantly lower serum glucose levels after insulin injection as compared with insulin injection alone. These data indicate that Mfge8 acutely modulates the glucose uptake response to insulin. Co-injection of αv or 05 integrin blocking antibodies with insulin may reduce insulin requirements by approximately 50%. Systemic therapy with αv or 05 integrin blocking antibodies may enhance insulin sensitivity in at-risk populations of individuals.

Glucose Uptake Assay.

Uptake of fatty acids by primary cells and cell lines was assessed using the fluorescent D-glucose analog 2-[N-(7-nitrobenz-2-oxa-1,3-diazol-4-yl)amino]-2-deoxy-D-glucose (2-NBDG) (Invitrogen). 2-NBDG has been successfully used as an alternative to 2-deoxyglucose in the measurement of glucose uptake in multiple cell types. Cells were plated in triplicate in 96-well plates at a concentration of 25,000 cells per well in 100 µl of DMEM/10% FCS. Plates were centrifuged at 1000 rpm for 4 minutes and incubated at 37° C. for 4-5 hours. Cells were then serum deprived for 1 hour before treatment with recombinant proteins for 20 minutes followed by the addition of 2-NBDG (100 µM) for 10 min at 37° C. in a humidified atmosphere of 5% $CO_2$. Reaction was stopped by adding a twofold volume of ice-cold PBS and the wells were washed again with ice-cold PBS three times. The fluorescent signal before (autofluorescence) and after adding 100 µM 2-NBDG was measured using fluorescent plate reader at 37° C. (Molecular Device using the 485 nmex and 520 nmemiss filter set). The net increase in fluorescence was normalized to the lowest signal (0 cells/well). In experiments using function-blocking antibodies, antibodies against mouse integrins αv (clone RMV-7), β (clone 2C9.G2; BD Biosciences), β5 (clone ALULA), β1 (clone HA2/5; BD Biosciences), anti-rat with cross-reactivity with mouse, were added to cells after serum deprivation and cells were incubated for 20 minutes prior to addition of recombinant proteins.

Insulin Tolerance Test.

Mice were fasted for 4 hours after which they were injected with 1.5 U/kg of insulin IP. Blood was collected from the tail vein immediately before injection and then again after 15, 30, 60, and 90 minutes for evaluation of blood glucose.

Blood Glucose Measurement.

In experiments using RGE or Mfge8 construct: mice received 50 µg/kg body weight of recombinant protein. In experiments using function-blocking antibodies: 6-8 week-old mice were fasted for 4 hours and then each mouse received 0.5 µg antibody (integrins αv (clone RMV-7) and β5 (clone ALULA)) per gram body weight in total volume of 200 µl, 15 minutes later each mouse received an insulin injection (1.5 U/kg, intraperitoneal injection (IP)). Blood glucose levels were measured by sampling from the tail vein of mice from 15 minutes after insulin administered.

Example: Mfge8 Modulates Glucose Uptake In Vitro and In Vivo

This example illustrates enhanced, antral smooth muscle contraction in Mfge8−/− mice. It also shows that PI3K inhibition prevented exaggerated Mfge8−/− antral ring contraction.

Figure 13:
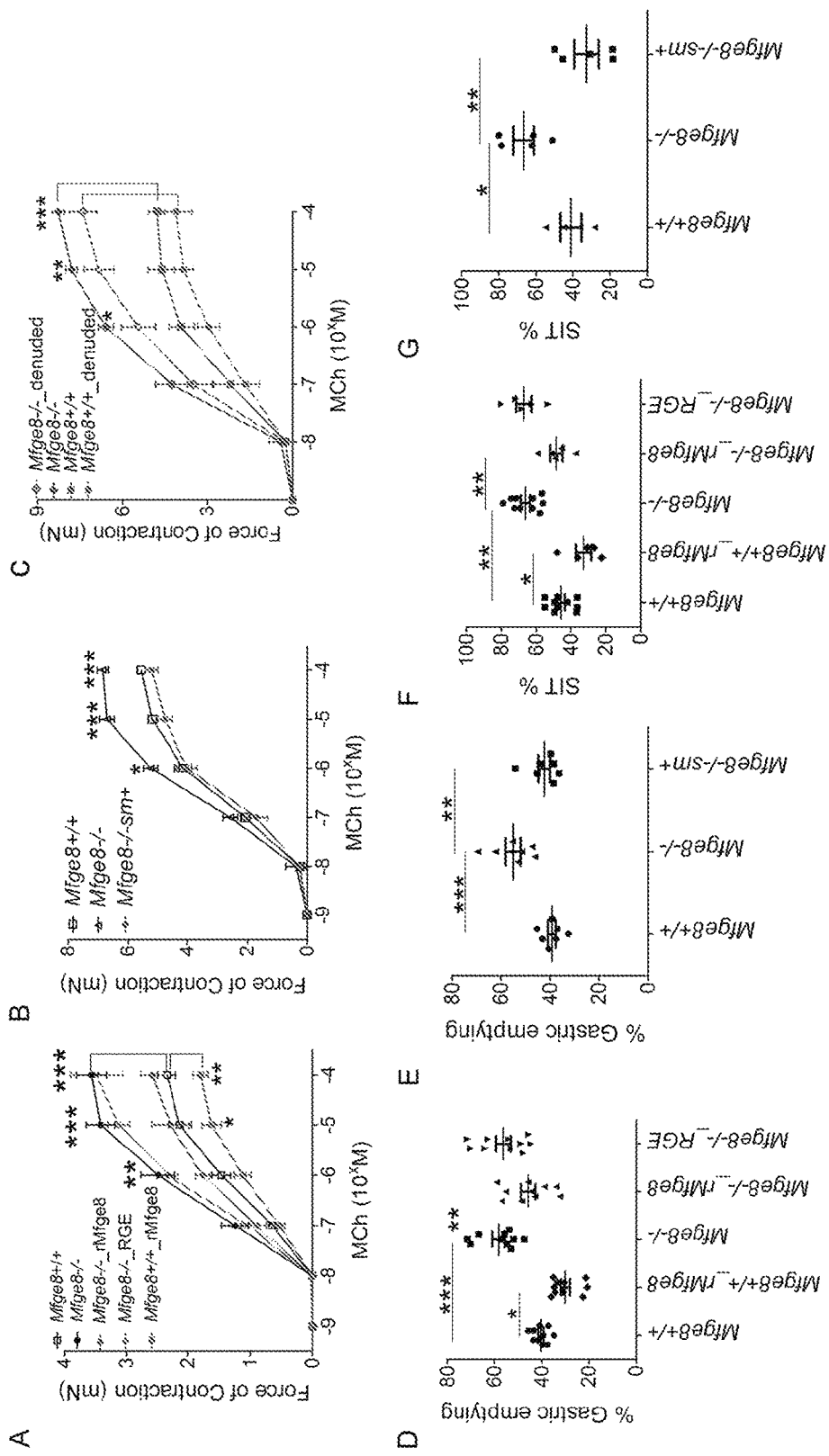
FIGS. 13A-13G. Enhanced, antral smooth muscle contraction in Mfge8−/− mice. (A-C) Force of antral smooth muscle ring contraction with and without the addition of rMfge8 or RGE construct (A) or after in vivo induction of transgenic Mfge8 expression in Mfge8−/−sm+ mice in response to MCh. (C) Force of antral contraction with and without epithelium (denuded). Mfge8−/− mice have enhanced gastric emptying and more rapid small intestine transit time (SIT). (D-E) Gastric emptying was measured by the proportion of phenol red remaining in the stomach 15 minutes after gavage. N=7-10. (F-G) Small intestinal transit times after gavage with Carmine dye with subsequent evaluation at 15 minutes of dye migration along the intestinal tract. N=5-10 in C and 3-5 in D. For FIGS. 13E and 13G, Mfge8−/−sm+ and single transgenic controls were placed on doxycycline for 2 weeks prior to the experiments to induce Mfge8 production in the smooth muscle. *P<0.05, P<0.01, *P<0.001.

FIGS. 13A-13C show the force of antral smooth muscle ring contraction with and without the addition of the rMfge8 or RGE construct (FIG. 13A) or after in vivo induction of transgenic Mfge8 expression in Mfge8−/−sm+ mice in response to MCh (FIG. 13B). FIG. 13C shows the force of antral contraction with and without epithelium (denuded). Mfge8−/− mice have enhanced gastric emptying and more rapid small intestine transit time (SIT). FIGS. 13D and 13E show that gastric emptying was measured by the proportion of phenol red remaining in the stomach 15 minutes after gavage. N=7-10. FIGS. 13F and 13G shows small intestinal transit times after gavage with Carmine dye with subsequent evaluation at 15 minutes of dye migration along the intestinal tract. N=5-10 in FIG. 13C and 3-5 in FIG. 13D. In FIGS. 13E and 13G, Mfge8−/−sm+ and single transgenic controls were placed on doxycycline for 2 weeks prior to the experiments to induce Mfge8 production in the smooth muscle. *P<0.05, P<0.01, *P<0.001.

Figure 14:
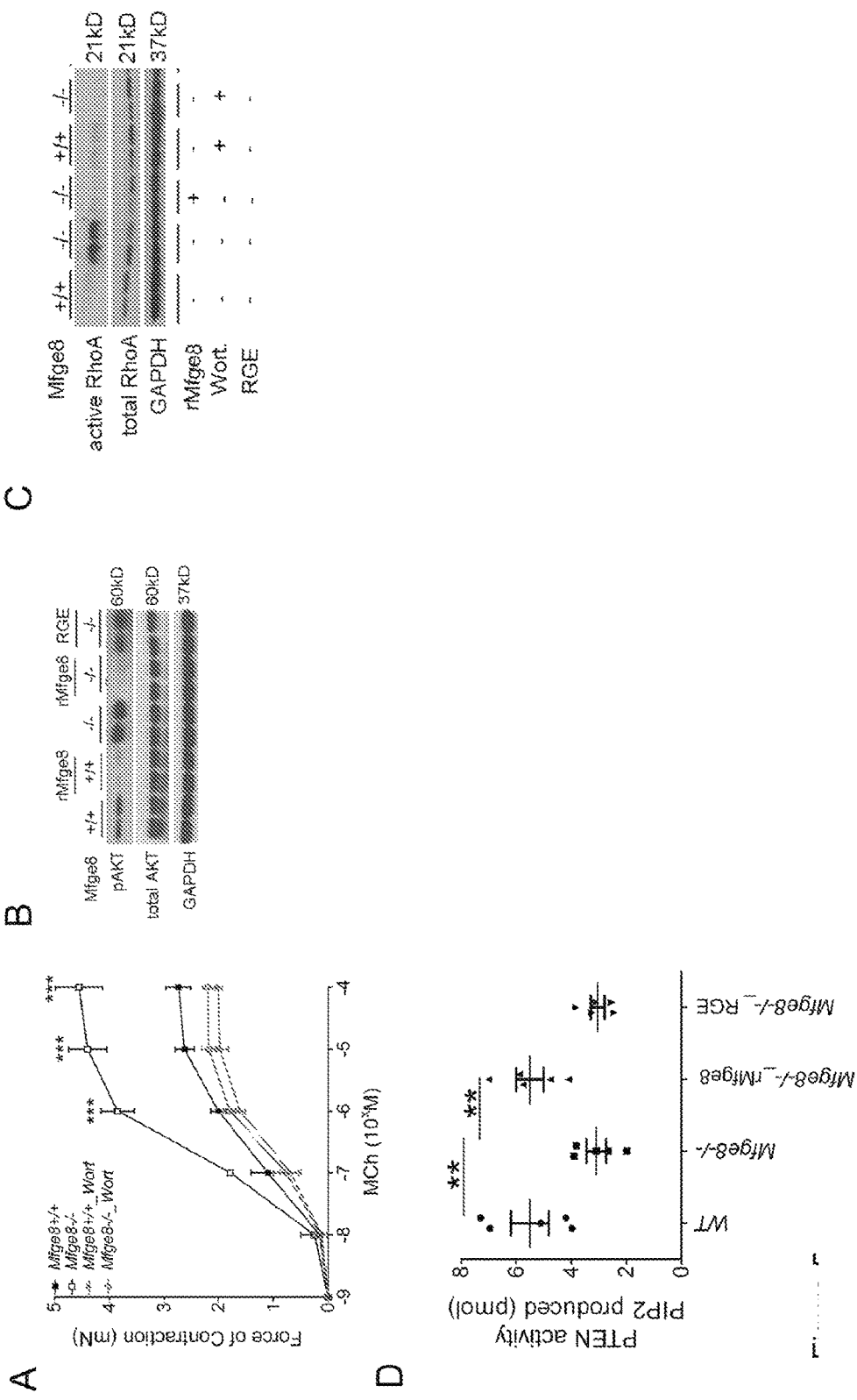
FIGS. 14A-14D. Inhibition of PI3K prevents exaggerated Mfge8−/− antral ring contraction. (A) Antral rings were treated for 15 min with PI3K inhibitor wortmannin (Wort.100 nm) followed by assessment of contractile force in response to MCh. N=3-4. ***P<0.0001. (B) Mfge8 reduces AKT phosphorylation. Western blot of antral tissue treated for 30 minutes with or without rMfge8. (C) Wortmannin prevents RhoA activation. Western blot of antrum treated for 30 minutes with wortmannin (100 ng/ml) or Mfge8 and then with MCh for 15 minutes prior to quantifying active RhoA using a GST pull-down. (D) Mfge8 modulates PTEN activity. PTEN activity assay measuring conversion of PIP3 to PIP2 in freshly isolated antrum with and without rMfge8 or RGE construct (10 µg/ml) n=3-5. *P<0.05, P<0.01, *P<0.001.

In FIG. 14A, the antral rings were treated for 15 min with PI3K inhibitor wortmannin (Wort.100 nm) followed by assessment of contractile force in response to MCh. N=3-4. *P<0.0001. FIG. 14B shows that Mfge8 reduces AKT phosphorylation. Western blot of antral tissue were treated for 30 minutes with or without rMfge8. FIG. 14C shows that wortmannin prevents RhoA activation. Western blot of antrum were treated for 30 minutes with wortmannin (100 ng/ml) or Mfge8 and then with MCh for 15 minutes prior to quantifying active RhoA using a GST pull-down. FIG. 14D** shows that Mfge8 modulates PTEN activity. PTEN activity assay measured the conversion of PIP3 to PIP2 in freshly isolated antrum with and without the rMfge8 or RGE construct (10 μg/ml) n=3-5. *P<0.05, P<0.01, *P<0.001.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of reducing fatty acid uptake and enhancing insulin sensitivity in an animal that is insulin resistant, the method comprising, administering an antagonist of integrin $\alpha_v\beta_5$ to an animal that has reduced insulin sensitivity in an amount sufficient to reduce fatty acid uptake in the animal and enhance insulin sensitivity, wherein the antagonist is an antibody that has the CDRs of ALULA, the antibody produced by the hybridoma deposited under ATCC Deposit No. PTA-5817;

thereby reducing fatty acid uptake and enhancing insulin sensitivity in the animal.

2. The method of claim 1, wherein the animal is a human.

3. The method of claim 1, wherein the antibody is a humanized or chimeric antibody.

4. The method of claim 1, wherein the animal is obese.

5. The method of claim 1, wherein the antagonist is administered intravenously, subcutaneously, intramuscularly, rectally, or orally.

6. The method of claim 1, wherein the antibody is a humanized version of the ALULA antibody.

* * * * *